(12) United States Patent
Yamasaki et al.

(10) Patent No.: US 6,242,474 B1
(45) Date of Patent: Jun. 5, 2001

(54) AROMATIC RING DERIVATIVES

(75) Inventors: Noritsugu Yamasaki, Hyogo; Takafumi Imoto; Takahiro Hiramura, both of Niigata; Osamu Onomura, Nagasaki; Masahiro Nishikawa, Niigata; Hiroshi Kayakiri, Osaka; Yoshito Abe, Ibaraki; Hitoshi Hamashima, Kyoto; Hitoshi Sawada, Ibaraki, all of (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/446,619

(22) PCT Filed: Jun. 26, 1998

(86) PCT No.: PCT/JP98/02886

§ 371 Date: Mar. 21, 2000

§ 102(e) Date: Mar. 21, 2000

(87) PCT Pub. No.: WO99/00359

PCT Pub. Date: Jan. 7, 1999

(30) Foreign Application Priority Data

Jun. 27, 1997 (JP) .................................................. 9-187849

(51) Int. Cl.$^7$ ..................... A61K 31/4164; C07D 233/56
(52) U.S. Cl. ................... 514/400; 548/338.5; 548/338.1; 548/335.1; 548/315.1; 514/399; 514/397
(58) Field of Search .................................... 514/400, 399, 514/397; 548/338.5, 338.1, 335.1, 315.1

(56) References Cited

U.S. PATENT DOCUMENTS

| 2,457,371 | 12/1948 | Hirt et al. . |
| 5,298,502 | 3/1994 | Halling et al. . |
| 5,824,657 | * 10/1998 | Hill et al. ............................... 514/46 |

FOREIGN PATENT DOCUMENTS

| 1 182 243 | 1/1963 | (DE) . |
| 0 507 594 A1 | 10/1992 | (EP) . |
| 0 882 718 A1 | 12/1998 | (EP) . |
| WO 96/03380 A1 | 2/1996 | (WO) . |
| WO 96/16046 | 5/1996 | (WO) . |
| WO 97/00863 | 2/1997 | (WO) . |
| WO 97/00864 | 2/1997 | (WO) . |
| WO 97/022586 | 6/1997 | (WO) . |
| WO 97/24334 | 7/1997 | (WO) . |

OTHER PUBLICATIONS

S. Sakurai et al., Pharmaceutical Society of Japan, vol. 117, No. 5, "Synthesis and dual antagonistic activity against thromboxane A2 and leukotriene D4 of benzenesulfonamide derivatives," pp. 298–318 (1997) Abstract XP002135537.

* cited by examiner

*Primary Examiner*—Charanjit S. Aulakh
(74) *Attorney, Agent, or Firm*—Foley & Lardner

(57) ABSTRACT

Novel aromatic ring derivatives represented by formula (I) or their pharmaceutical acceptable salts are provided.

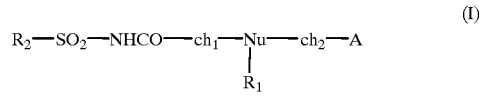

wherein Nu represents a 5- or 6-membered aromatic ring; $ch_1$ and $ch_2$ each represents a cross-linking group; and A represents an aromatic ring.

These compounds have blood sugar-depressing activity or PDE 5 inhibitory activity and are useful as medicines for treating impaired glucose tolerance, diabetes, diabetic complications, syndrome of insulin-resistance, polycystic ovary syndrome, hyperlipidemia, atherosclerosis, cardiovascular disorders, hyperglycemia, hypertension, stenocardia, pulmonary hypertension, congestive heart failure, glomerulopathy, tubulointerstitial disorders, renal failure, angiostenosis, distal angiopathy, cerebral apoplexy, chronic reversible obstructions, autoimmune diseases, allergic rhinitis, urticaria, glaucoma, diseases characterized by enteromotility disorders, impotence, nephritis, cachexia, pancreatitis, restenosis after PTCA, etc.

10 Claims, 3 Drawing Sheets

(31)

(32)

(33)

(34)

(35)

(36)

(37)

(38)

(39)

(40)

(41)

(42)

(43)

(44)

(45)

AROMATIC RING DERIVATIVES

This application is a 371 of PCT/JP98/02886, May 25, 1998, now WO99/00359, Jan. 7, 1999.

TECHNICAL FIELD

The present invention relates to novel aromatic ring derivatives and specifically to novel aromatic ring derivatives and their pharmaceutically acceptable salts having blood sugar level-depressing activity or PDE5-inhibiting activity. The present invention also relates to pharmaceutical compositions comprising such an aromatic ring derivative or its salt as an active ingredient.

DISCLOSURE OF THE INVENTION

An objective of the present invention is to provide novel aromatic ring derivatives and their pharmaceutically acceptable salts, and also pharmaceutical compositions comprising such an aromatic ring derivative or its pharmaceutically acceptable salt as an active ingredient, which are useful for preventing and treating impaired glucose tolerance, diabetes (type II diabetes), diabetic complications (e.g., diabetic gangrene, diabetic arthropathy, diabetic osteopenia, diabetic glomerulosclerosis, diabetic nephropathy, diabetic dermatopathy, diabetic neuropathy, diabetic cataract, diabetic retinopathy, etc.), syndrome of insulin resistance (e.g., insulin receptor disorders, Rabson-Mendenhall syndrome, leprechaunism, Kobberling-Dunnigan syndrome, Seip syndrome, Lawrence syndrome, Cushing syndrome, acromegaly, etc.), polycystic ovary syndrome, hyperlipidemia, atherosclerosis, cardiovascular disorders (e.g., stenocardia, cardiac failure, etc.), hyperglycemia (e.g., those characterized by abnormal saccharometabolism such as feeding disorders, etc.), hypertension, stenocardia, pulmonary hypertension, congestive heart failure, glomerulopathy (e.g., diabetic glomerulosclerosis, etc.), tubulointerstitial disorders (e.g., renopathy induced by FK506, cyclosporin, etc.), renal failure, atherosclerosis, angiostenosis (e.g., after percutaneous arterioplasty), distal angiopathy, cerebral apoplexy, chronic reversible obstructions (e.g., bronchitis, asthma (chronic asthma, allergic asthma), etc.), autoimmune diseases, allergic rhinitis, urticaria, glaucoma, diseases characterized by enteromotility disorders (e.g., hypersensitive enteropathy syndrome, etc.), impotence (e.g., organic impotence, psychic impotence, etc.), nephritis, cachexia (e.g., progressive weight loss due to lipolysis, myolysis, anemia, edema, anorexia etc., in chronic diseases including cancer, tuberculosis, endocrinopathy, AIDS, etc.), pancreatitis, or restenosis after PTCA.

The present inventors provide novel aromatic ring derivatives represented by any one of formulae (I) and (III) to (VI) below and their pharmaceutically acceptable salts, and also provide pharmaceutical compositions comprising the compound as an active ingredient, which are useful for preventing and treating impaired glucose tolerance, diabetes (type II diabetes), diabetic complications (e.g., diabetic gangrene, diabetic arthropathy, diabetic osteopenia, diabetic glomerulosclerosis, diabetic nephropathy, diabetic dermatopathy, diabetic neuropathy, diabetic cataract, diabetic retinopathy, etc.), syndrome of insulin resistance (e.g., insulin receptor disorders, Rabson-Mendenhall syndrome, leprechaunism, Kobberling-Dunnigan syndrome, Seip syndrome, Lawrence syndrome, Cushing syndrome, acromegaly, etc.), polycystic ovary syndrome, hyperlipidemia, atherosclerosis, cardiovascular disorders (e.g., stenocardia, cardiac failure, etc.), hyperglycemia (e.g., those characterized by abnormal saccharometabolism such as feeding disorders, etc.), hypertension, stenocardia, pulmonary hypertension, congestive heart failure, glomerulopathy (e.g., diabetic glomerulosclerosis, etc.), tubulointerstitial disorders (e.g., renopathy induced by FK506, cyclosporin, etc.), renal failure, atherosclerosis, angiostenosis (e.g., after percutaneous arterioplasty), distal angiopathy, cerebral apoplexy, chronic reversible obstructions (e.g., bronchitis, asthma (chronic asthma, allergic asthma), etc.), autoimmune diseases, allergic rhinitis, urticaria, glaucoma, diseases characterized by enteromotility disorders (e.g., hypersensitive enteropathy syndrome, etc.), impotence (e.g., organic impotence, psychic impotence, etc.), nephritis, cachexia (e.g., progressive weight loss due to lipolysis, myolysis, anemia, edema, anorexia etc., in chronic diseases including cancer, tuberculosis, endocrinopathy, AIDS, etc.), pancreatitis, or restenosis after PTCA.

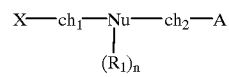

(I)

wherein X indicates a substituent represented by formula (II):

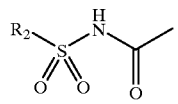

(II)

wherein $R_2$ represents a lower alkyl group, a lower alkenyl group, a lower alkynyl group, a cyclo-lower alkyl group, an aromatic group, or a heterocyclic group, each of which may have one or more substituents; $ch_1$ and $ch_2$ each represents a saturated or unsaturated cross-linking group, which may be branched; $ch_1$ may have one or more substituents selected from the group consisting of a lower alkyl group, a lower cycloalkyl group, an aromatic group, a heterocyclic group, a lower alkyl-lower cycloalkyl group, an aromatic-lower alkyl group, and a heterocyclic-lower alkyl group; Nu represents a 5- or 6-membered aromatic group; X and Nu may be bonded directly to each other; $R_1$ represents a hydrogen atom, a halogen atom, a lower alkyl group, an amino group, an acylamino group, a lower alkenyl group, a lower alkynyl group, a halo-lower alkyl group, a lower cycloalkyl group, a nitro group, a lower alkylamino group, a carboxyl group, an esterified carboxyl group, an amidated carboxyl group, a lower alkanesulfonyl group, an aromatic-sulfonyl group, a hydroxyl group, or a lower alkoxyl group; n is a natural number of 2 or less; and A is an aromatic ring that may have one or more substituents.

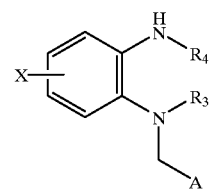

(III)

wherein $R_3$ represents a hydrogen atom or a lower alkyl group; $R_4$ represents a hydrogen atom or an acyl group; X and A are as defined above.

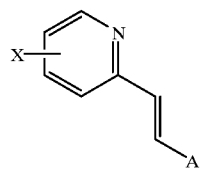

(IV)

wherein A is as defined above.

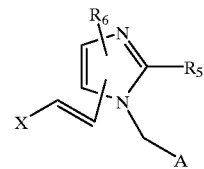

(V)

wherein $R_5$ represents a hydrogen atom or a lower alkyl group; $R_6$ represents a hydrogen atom, a halogen atom, or a phenyl group; and X and A are as defined above.

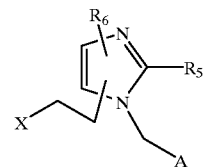

(VI)

wherein A, $R_5$, and $R_6$ are as defined above.

The aromatic ring derivatives of the present invention in which Nu is a benzene ring can be synthesized through the reaction scheme represented by formulae (a) to (h) below.

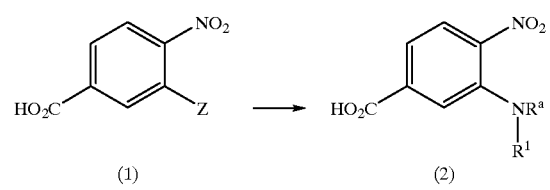

(a)

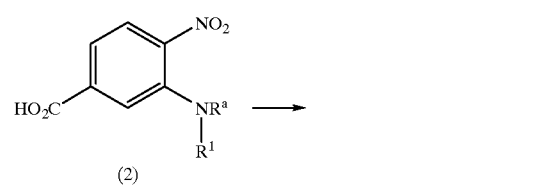

(b)

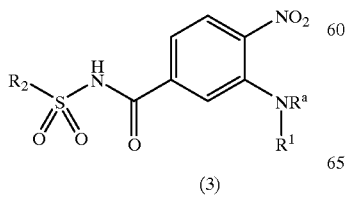

(3)

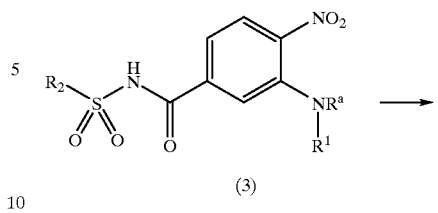

(c)

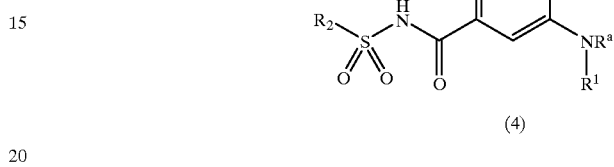

(4)

In formulae (a) to (c), Z represents a halogen atom; $R^1$ has the same definition as $CH_2A$ described above; $R^a$ represents a hydrogen atom or an alkyl group; $R_2$ is a alkyl group, a lower alkenyl group, a lower alkynyl group, a cyclo-lower alkyl group, an aromatic group, or a heterocyclic group, which may have one or more substituents.

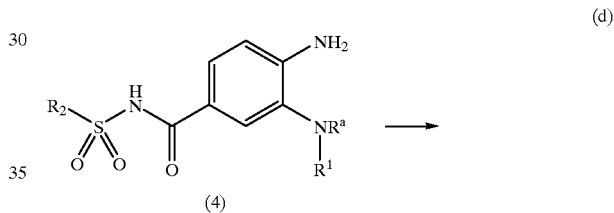

(d)

(5)

In formula (d), $R^1$ and $R_2$ are as defined above, and $R^a$ and $R^b$ represent a hydrogen atom or an alkyl group.

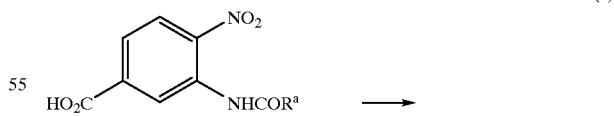

(e)

(6)

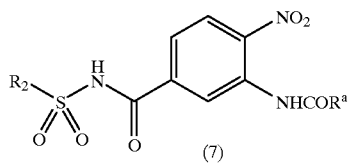

(7)

-continued

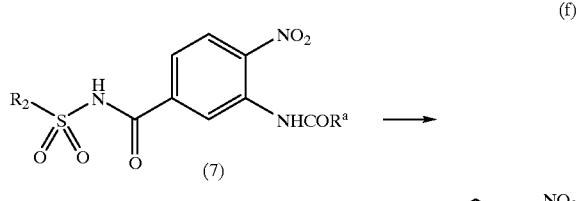
(f)

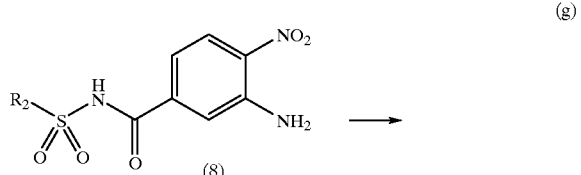

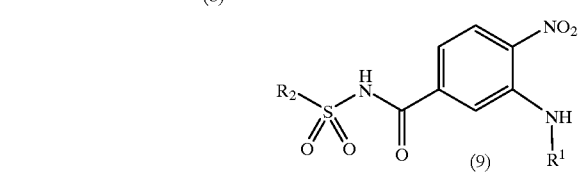

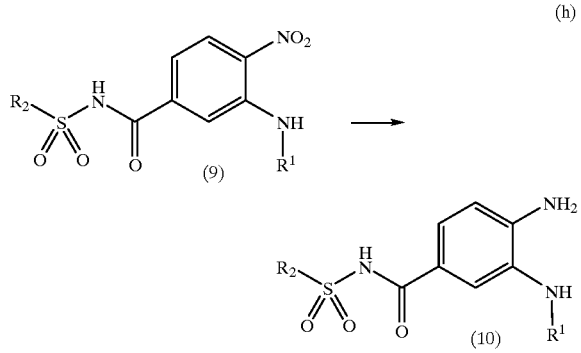

In formulae (e) to (h), R¹ and R₂ are as defined above, and $R^a$ represents a hydrogen atom or an alkyl group.

In formula (a) the compound of formula (2) can be synthesized from the compound of formula (1) and $R^1NHR^a$, wherein $R^a$ and $R^1$ are as defined above. In formula (b), the compound of formula (3) can be obtained by reacting the compound of formula (2) with a carboxylic acid-activating agent, such as N,N'-carbonyldiimidazole, 1-(3-dimethylaminopropyl)-3-ethylcarbodiimide or its salts, dicyclohexylcarbodiimide, isobutyloxycarbonyl chloride, isobutyloyl chloride, pivaloyl chloride, isobutylchloroformate, diphenylphosphoryl azide, or diethyl cyanophosphate, and then reacting the reaction product with the corresponding sulfonamides in the presence of a base, such as diazabicycloundecene, triethylamine, 4-dimethylaminopyridine, N,N-dimethylaniline, pyridine, N-methylmorpholine, N-ethylpiperidine, potassium hydroxide, sodium hydroxide, potassium phosphate, potassium hydrogen carbonate, potassium carbonate, sodium carbonate, sodium hydride, potassium t-butoxide, sodium methoxide, or sodium ethoxide.

In formula (c), the compound of formula (4) can be obtained by reducing the nitro group of the compound of formula (3) with a hydrogenation catalyst such as palladium-carbon in a hydrogen atmosphere. The nitro group can also be reduced with 1) reduced iron or zinc, 2) sodium hydrosulfite, 3) formic acid or ammonium formate in the presence of a transition metal catalyst such as palladium-carbon; 4) with nickel; etc.

The compound of formula (5) can be produced from the compound of formula (4) through the reaction of formula (d). Specifically, the compound of formula (4) is allowed to react with $R^bCOY$ ($R^b$ represents a hydrogen atom or an alkyl group, and Y is a chlorine atom or a bromine atom) in the presence of a base to obtain the compound of formula (5).

In formula (e), the compound of formula (6) can be converted to the compound of formula (7) in the same manner as in the reaction of formula (b). In formula (f), the compound of formula (7) can be hydrolyzed with a base, such as lithium hydroxide, sodium hydroxide, potassium hydroxide, potassium carbonate, or sodium carbonate, to give the compound of formula (8). In formula (g), the compound of formula (9), corresponding to the compound of formula (3) in which $R^a$ is a hydrogen atom, can be synthesized from the compound of formula (8) and a compound of the formula $R^1Z'$ ($R^1$ is as defined above, and Z' represents a chlorine atom, a bromine atom, an iodine atom, an alkanesulfonyl group, or an arylsulfonyl group) in the presence of a base. In formula (h), the compound of formula (9) can be converted into the compound of formula (10) that is the compound of formula (4) in which $R^a$ is a hydrogen atom in the same manner as in formula (c).

When Nu is a pyridine ring in the compound of formula (I), aromatic ring derivatives of the present invention can be synthesized through the reaction scheme represented by formulae (i) to (k).

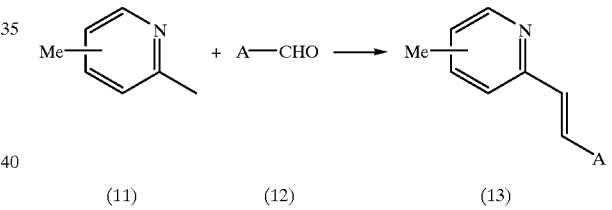

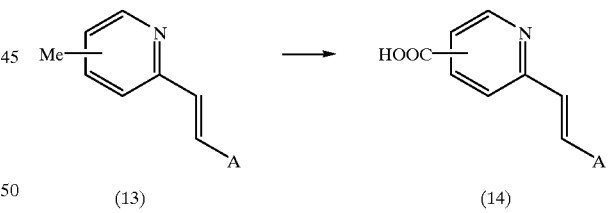

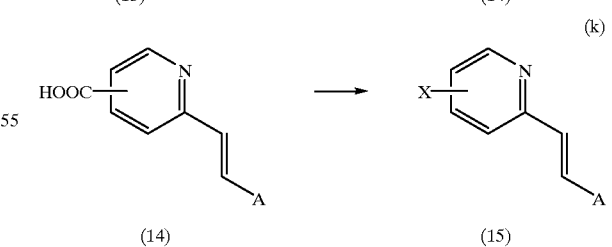

In formulae (i) to (k), A is as defined above.

The compound of formula (13) can be synthesized from compounds of formulae (11) and (12) in acetic anhydride according to formula (i). In formula (j), the compound of formula (14) can be produced by reacting the compound of formula (13) with selenium dioxide in the presence of a base such as pyridine or the like. In formula (k), the compound of formula (15) can be obtained from the compound of formula (14) in the same manner as in formula (b).
When Nu is an imidazole ring in the compound of formula (I), aromatic ring derivatives of the present invention can be synthesized according to the reaction scheme represented by formulae (1) to (x) below.
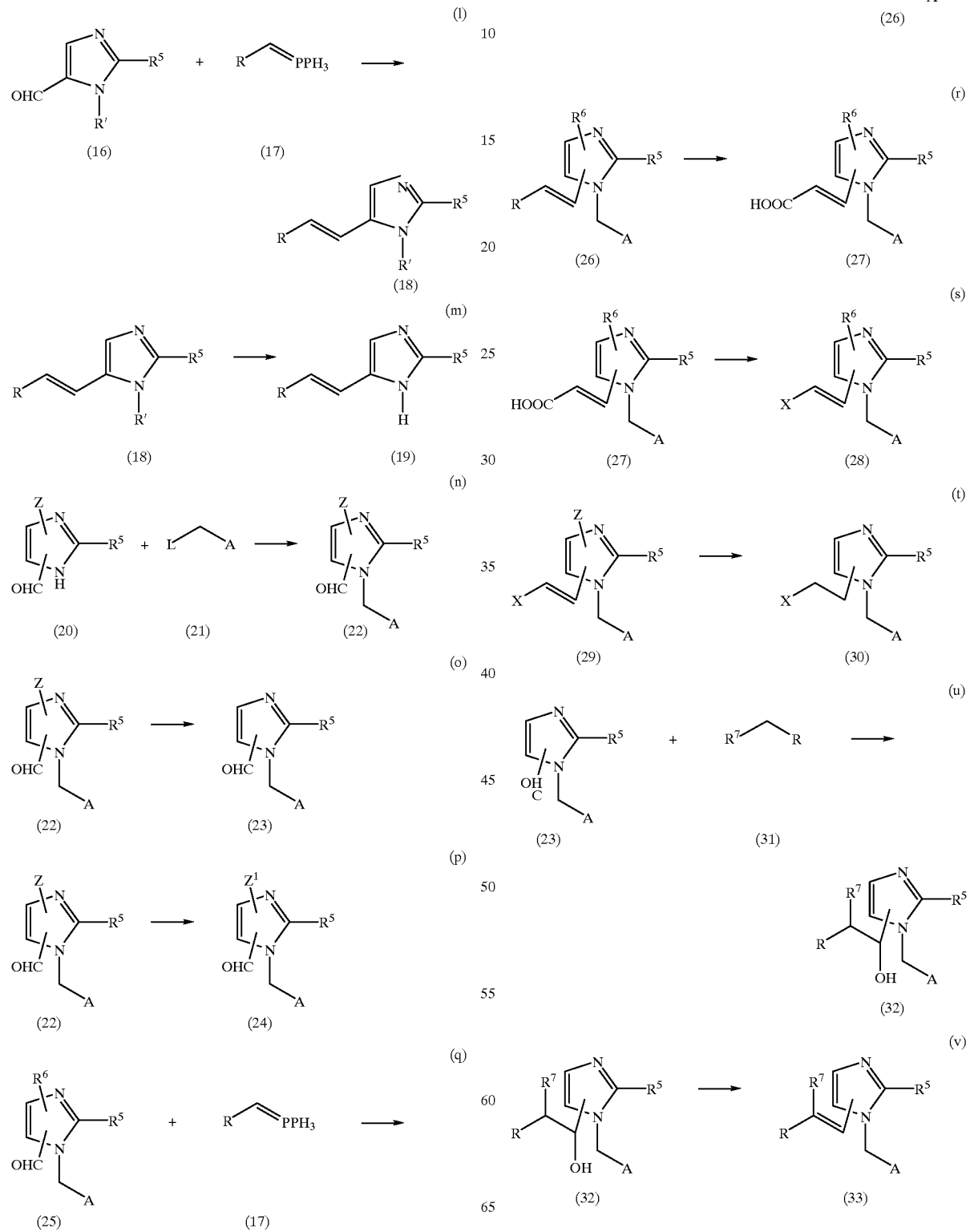

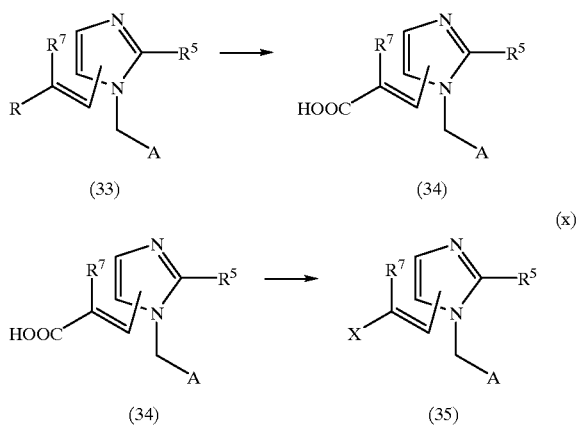

In formulae (1) to (x), $R^5$ represents a hydrogen atom or a lower alkyl group; $R^6$ represents a hydrogen atom, a halogen atom, or a phenyl group; $R^7$ is an aromatic-lower alkyl group; X and A are as defined above; Z is a halogen atom; $Z^1$ represents a phenyl group; L represents a leaving group such as a halogen atom or the like; Ph is a phenyl group; R represents a protected carboxylic acid; R' is an imino-protecting group.

In formula (1), the compound of formula (16) can be allowed to react with the compound of formula (17) to obtain the compound of formula (18). In formula (m), the imino-protecting group in the compound of formula (18) is eliminated by, for example, reacting the compound of formula (19) with hydrogen chloride in alcohol, to give the compound of formula (19). In formula (n), the compound of formula (22) can be obtained by reacting the compound of formula (20) with the compound of formula (21) in the presence of a base such as sodium hydride. In formula (o), the compound of formula (23) can be produced by subjecting the compound of formula (22) to dehalogenation by, for example, catalytic reduction. In formula (p), the compound of formula (24) can be obtained by reacting the compound of formula (22) with phenylboric acid in the presence of a metal catalyst such as tetrakis(triphenylphosphine)palladium(0), and a base such as sodium carbonate. In formula (q), the compound of formula (26) can be synthesized from the compound of formula (25) in the same manner as in formula (1). In formula (r), the carboxy-protecting group in the compound of formula (26) can be eliminated by, for example, hydrolysis, to obtain the compound of formula (27). In formula (s), the compound of formula (28) can be produced from the compound of formula (27) in the same manner as in formula (b). In formula (t), the compound of formula (30) can be obtained by subjecting the compound of formula (29) to reduction reaction, such as catalytic reduction.

In formula (u), the compound of formula (32) can be obtained from the compounds of formulae (23) and (31) in the presence of a base such as lithium diisopropylamide, sodium amide, potassium t-butoxide, sodium methoxide, sodium hydroxide, or potassium hydroxide. The compound of formula (32) can be converted into the compound of formula (33) using an acid or a base. Alternatively, the hydroxyl group in the compound of formula (32) can be converted to a leaving group such as an acyloxy group, a methanesulfonyloxy group, a toluenesulfonyloxy group, or a trifluoromethanesulfonyloxy group prior to the reaction with an acid or a base, to obtain the compound of formula (33) under a milder reaction condition. The compound of formula (33) can also be obtained from the compound of formula (32) by using a dehydration agent (formula (v)). In reaction formula (w), the carboxy-protecting group of the compound of formula (33) can be eliminated by, for example, hydrolysis to give the compound of formula (34). In formula (x), the compound of formula (35) is obtainable from the compound of formula (34) in the same manner as in formula (b). The compound of formula (26) can be obtained from the compound of formula (25) and the compound of formula (31) represented by $CH_3R$ (R is as defined above) in the same manner as in formulae (u) and (v).

If desired, any of the reaction intermediates formed in the above-described reaction steps can be purified, prior to being subjected to the next step, by conventional purification methods usually used in chemical synthesis, including, for example, recrystallization, column chromatography, thin-layer chromatography, high-performance liquid chromatography, and the like. The final product, which is the compound of the present invention, can also be purified by conventional methods for purifying organic compounds, including, for example, recrystallization, column chromatography, thin-layer chromatography, high-performance liquid chromatography, and the like. The compounds can be identified by NMR spectrography, mass spectrography, IR spectrography, elemental analysis, measurement of melting point, and the like.

Preferred embodiments of various definitions fallen within the scope of the present invention used herein are described in detail below.

Unless otherwise specified, the term "lower" means 1 to 6 carbon atoms. Examples of the lower alkyl group include linear or branched alkyl groups such as a methyl group, an ethyl group, an n-propyl group, an i-propyl group, an n-butyl group, an i-butyl group, a sec-butyl group, a t-butyl group, an n-pentyl group, an i-pentyl group, a sec-pentyl group, a t-pentyl group, a 2-methylbutyl group, an n-hexyl group, a 1-methylpentyl group, a 2-methylpentyl group, a 3-methylpentyl group, a 4-methylpentyl group, a 1-ethylbutyl group, a 2-ethylbutyl group, a 1,1-dimethylbutyl group, a 2,2-dimethylbutyl group, a 3,3-dimethylbutyl group, a 1-ethyl-1-methyl propyl group, etc. An alkyl group having 1 to 3 carbon atoms is preferred.

The halogen atom includes a fluorine atom, a chlorine atom, a bromine atom, and an iodine atom. A fluorine atom, a chlorine atom, and a bromine atom are preferred.

The halo-lower alkyl group means a linear or branched alkyl group having up to 8 carbon atoms, which is substituted with one or more halogen atoms selected from fluorine, chlorine, bromine, and iodine. A linear or branched alkyl group having up to 8 carbon atoms, which is substituted with one or more halogen atoms selected from fluorine, chlorine, and bromine is preferred. A linear or branched alkyl group having 1 to 3 carbon atoms is more preferred. Examples thereof include a fluoromethyl group, a difluoromethyl group, a trifluoromethyl group, a chloromethyl group, a dichloromethyl group, a trichloromethyl group, a bromomethyl group, a dibromomethyl group, a tribromomethyl group, a 1-fluoroethyl group, a 1-chloroethyl group, a 1-bromoethyl group, a 2-fluoroethyl group, a 2-chloroethyl group, a 2-bromoethyl group, a 1,2-difluoroethyl group, a 1,2-dichloroethyl group, a 1,2-dibromoethyl group, a 2,2,2-trifluoroethyl group, a heptafluoroethyl group, a 1-fluoropropyl group, a 1-chloropropyl group, a 1-bromopropyl group, a 2-fluoropropyl group, a 2-chloropropyl group, a 2-bromopropyl group, a 3-fluoropropyl group, a 3-chloropropyl group, a 3-bromopropyl group, a 1,2-difluoropropyl group, a 1,2-dichloropropyl group, a 1,2-dibromopropyl group, a 2,3-difluoropropyl group, a 2,3-dichloropropyl group, a 2,3-dibromopropyl group, a 3,3,3-trifluoropropyl group, a 2,2,3,3,3-pentafluoropropyl group, a 2-fluorobutyl group, a 2-chlorobutyl group, a 2-bromobutyl group, a 4-fluorobutyl group, a 4-chlorobutyl group, a 4-bromobutyl group, a 4,4,4-trifluorobutyl group, a 2,2,3,3,4,4,4-heptafluorobutyl group, a perfluorobutyl group, a 2-fluoropentyl group, a 2-chloropentyl group, a 2-bromopentyl group, a 5-fluoropentyl group, a 5-chloropentyl group, a 5-bromopentyl group, a perfluoropentyl group, a 2-fluorohexyl group, a 2-chlorohexyl group, a 2-bromohexyl group, a 6-fluorohexyl group, a 6-chlorohexyl group, a 6-bromohexyl group, a perfluorohexyl group, a 2-fluoroheptyl group, a 2-chloroheptyl group, a 2-bromoheptyl group, a 7-fluoroheptyl group, a 7-chloroheptyl group, a 7-bromoheptyl group, a perfluoroheptyl group, etc.

The lower alkoxy group means a linear or branched alkyloxy group having up to 6 carbon atoms. Examples thereof include a methoxy group, an ethoxy group, an n-propyloxy group, an i-propyloxy group, an n-butyloxy group, an i-butyloxy group, a sec-butyloxy group, a t-butyloxy group, an n-pentyloxy group, an i-pentyloxy group, a sec-pentyloxy group, a t-pentyloxy group, a 2-methylbutoxy group, an n-hexyloxy group, an i-hexyloxy group, a t-hexyloxy group, a sec-hexyloxy group, a 2-methylpentyloxy group, a 3-methylpentyloxy group, a 1-ethylbutyloxy group, a 2-ethylbutyloxy group, a 1,1-dimethylbutyloxy group, a 2,2-dimethylbutyloxy group, a 3,3-dimethylbutyloxy group, a 1-ethyl-1-methylpropyloxy group, etc. Preferred are a methoxy group, an ethoxy group, an n-propyloxy group, an i-propyloxy group, an n-butyloxy group, an i-butyloxy group, a sec-butyloxy group, a t-butyloxy group, etc. An alkoxy group having 1 to 3 carbon atoms is preferred.

The lower cycloalkyl group means a cycloalkyl group having from 3 to 7 carbon atoms and preferably includes a cyclopropyl group, a cyclobutyl group, a cyclopentyl group, a cyclohexyl group, a cycloheptyl group, etc. A cycloalkyl group having 1 to 4 carbon atoms such as a cyclopropyl group and a cyclobutyl group is more preferred.

The lower alkyl-lower cycloalkyl group means a lower cycloalkyl group described above to which the above-described lower alkyl group is bonded.

Preferable examples of the lower alkenyl group include linear or branched lower alkenyl groups such as an ethenyl group, a 1-propenyl group, a 2-propenyl group, a 1-butenyl group, a 2-butenyl group, a 3-butenyl group, a 1,3-butadienyl group, a 1-pentenyl group, a 2-pentenyl group, 3-pentenyl group, a 4-pentenyl group, a 1-hexenyl group, a 2-hexenyl group, 3-hexenyl group, 4-hexenyl group, a 5-hexenyl group, a 1,4-methylpentenyl group, etc.

Preferable examples of the lower alkynyl group as include linear or branched lower alkynyl groups such as an ethynyl group, a 1-propynyl group, a 2-propynyl group, a 1-butynyl group, a 2-butynyl group, a 3-butynyl group, a 1-pentynyl group, a 2-pentynyl group, 3-pentynyl group, a 4-pentynyl group, a 2-methyl-3-butynyl group, a 1,1-dimethyl-2-butynyl group, a 5-hexynyl group, etc.

The saturated or unsaturated cross-linking group, which may be branched, means a substituent capable of serving as a cross-linking group, including a lower alkylene group, a lower alkenylene group, an oxy group, an oxy-lower alkyl group, a lower alkyloxy group, a carbonyl group, a lower alkenyl group, an imino group, an imino-lower alkyl group, a lower alkylimino group, a thio-lower alkyl group, a lower alkylthio group, etc., which may be substituted with a lower alkyl group, a lower cycloalkyl group, a lower alkyl-cycloalkyl group, an aromatic-lower alkyl group, or a heterocyclic-lower alkyl group. A methylene group, an ethylene group, an ethenylene group, an iminomethylene group, an N-methyl-iminomethylene group, etc. are preferable.

The lower alkylamino group means a linear or branched alkylamino group having up to 6 carbon atoms. Examples thereof includes a methylamino group, an ethylamino group, an n-propylamino group, an i-propylamino group, an n-butylamino group, an i-butylamino group, a sec-butylamino group, a t-butylamino group, an n-pentylamino group, an i-pentylamino group, a sec-pentylamino group, a t-pentylamino group, a 2-methylbutylamino group, an n-hexylamino group, a 1-methylpentylamino group, a 2-methylpentylamino group, a 3-methylpentylamino group, a 4-methylpentylamino group, a 1-ethylbutylamino group, a 2-ethylbutylamino group, a 3-ethylbutylamino group, a 1,1-dimethylbutylamino group, a 2,2-dimethylbutylamino group, a 3,3-dimethylbutylamino group, a 1-ethyl-1-methylpropylamino group, etc. Preferable examples are a lower alkylamino group having 1 to 4 carbon atoms, including a methylamino group, an ethylamino group, an n-propylamino group, an i-propylamino group, an n-butylamino group, an i-butylamino group, a sec-butylamino group, and a t-butylamino group.

The lower alkanesulfonyl group means a linear or branched alkanesulfonyl group whose alkyl moiety has up to 6 carbon atoms. Examples includes a methanesulfonyl group, an ethanesulfonyl group, a 1-propanesulfonyl group, a 2-propanesulfonyl group, a 1-butanesulfonyl group, a 2-butanesulfonyl group, a 1,1-dimethylethanesulfonyl group, a 1-(2-methylpropane)sulfonyl group, a n-pentanesulfonyl group, a 2-pentanesulfonyl group, a 3-pentanesulfonyl group, a 1-(3-methylbutane)sulfonyl group, a 1,1-dimethylpropanesulfonyl group, a 1-hexanesulfonyl group, a 2-hexanesulfonyl group, a 3-hexanesulfonyl group, a 1-(2-methylpentane)sulfonyl group, a 1-(3-methylpentane)sulfonyl group, a 1-(4-methylpentane)sulfonyl group, a 2-ethylbuthanesulfonyl group, a 3-ethylbutanesulfonyl group, a 1,1-dimethylbutanesulfonyl group, a 2,2-dimethylbutanesulfonyl group, a 3,3-dimethylbutanensulfonyl group, a 1-ethyl-1-methylpropanesulfonyl group, etc. An alkylsulfonyl group having 1 to 4 carbon atoms is preferred.

The 5- or 6-membered aromatic group is an aromatic group including, for example, a cyclopentadienyl group, a pyrrolyl group, a pyrazolyl group, an imidazolyl group, a phenyl group, a pyridyl group, a pyrimidinyl group, a pyridazinyl group, an furyl group, a pyranyl group, a triazolyl group, a tetrazolyl group, a thiophenyl group, etc.

The aromatic group means an aryl group or a heterocyclic aromatic group. The aryl group used herein means that having 6 to 10 carbon atoms. Examples thereof include a phenyl group, a naphthyl group, etc., and the term "naphthyl" used herein includes a 1-naphthyl group and a 2-naphthyl group. The heterocyclic aromatic ring means an unsaturated mono- or polycyclic hetero ring containing at least one hetero atom such as an oxygen atom, a sulfur atom, or a nitrogen atom. Examples of the heterocyclic aromatic ring include a pyrrolyl group, an imidazolyl group, a furyl group, a thienyl group, a thiazolyl group, a pyridyl group, a benzimidazolyl group, a benzofuryl group, an indolyl group, a benzothienyl group, a quinolyl group, an isoquinolyl group, a thiophenyl group, a furanyl group, etc. It may contain any substituents of the above-mentioned groups such as a halogen atom, a lower alkyl group, a cyano group, a nitro group, a trifluoromethyl group, a phenyl group, a halophenyl group, a heterocyclic group, a halo-heterocyclic group, etc. on its benzene or naphthalene ring. The position of the hetero atom in the aromatic ring is not particularly limited.

The aromatic-lower alkyl group means the above-described lower alkyl group bonded to the aromatic group described above. Examples thereof include a benzyl group, a 1-phenylethyl group, a 2-phenylethyl group, a phenylpropyl group, a phenylbutyl group, a phenylpentyl group, a phenylhexyl group, a naphthylmethyl group, a naphthylethyl group, a naphthylpropyl group, a naphthylbutyl group, a naphthylpentyl group, a naphthylhexyl group, a pyridylmethyl group, a pyridylethyl group, a quinolylmethyl group, isoquinolylmethyl group, a furanylmethyl group, etc., which may have one or more substituents on its aromatic ring; the substituents are the same as those described for the aromatic group.

The aromatic-sulfonyl group includes sulfonyl groups bonded to the above-described aromatic ring. Examples are a benzenesulfonyl group, a toluenesulfonyl group, naphthalenesulfonyl group, etc.

The heterocyclic group includes, for example, a pyridyl group, a quinolyl group, an isoquinolyl group, a thiazolyl group, a thiadiazolyl group, a benzofuranyl group, a dibenzofuranyl group, a thianaphthalenyl group, a 1H-1,2,3-triazolyl group, a 1,2,4-triazolyl group, a tetrazolyl group, a furyl group, a thienyl group, a pyrrolyl group, an imidazolyl group, a pyrimidinyl group, an indolyl group, a benzimidazolyl group, etc. These heterocyclic group may optionally be substituted by one or more substituents including halogen atoms and lower alkyl groups as those described above, and the substituted heterocyclic group includes, for example, a haloisoquinolyl group and a methylisoquinolyl group.

The halo-heterocyclic group means the above-described heterocyclic group bonded to the halogen atom described above.

The heterocyclic lower alkyl group means a lower alkyl group described above substituted by a heterocyclic group described above, including a pyridylmethyl group, etc. The halo-heterocyclic lower alkyl group is a heterocyclic lower alkyl group described above whose heterocyclic moiety is substituted with one or more halogens.

The term "pyridyl" used herein includes 2-pyridyl, 3-pyridyl, and 4-pyridyl, and its bonding position is not particularly limited. The bonding positions of the other heterocyclic groups are not also particularly limited.

A suitable heterocyclic group means a saturated or unsaturated mono- or polycyclic hetero ring containing at least one hetero atom such as an oxygen atom, a sulfur atom, a nitrogen atom, etc.

More preferable examples thereof include the following heterocyclic groups:

- 7- to 12-membered, preferably 9- or 10-membered unsaturated condensed heterocyclic group (preferably bicyclic group) having 1 to 5 nitrogen atoms, such as indolyl, isoindolyl, indolidinyl, benzimidazolyl, quinolyl, isoquinolyl, indazolyl, benzotriazolyl, tetrazolopyridyl, tetrazolopyridazinyl (e.g. tetrazolo[1, 5-b]pyridazinyl, etc.), dihydrotriazolopyridazinyl, or the like;
- 7- to 12-membered, preferably 9- or 10-membered unsaturated condensed heterocyclic group (preferably bicyclic group) having 1 to 3 sulfur atoms or S,S-dioxide thereof, such as dithianaphthalenyl (e.g. 4H-1,3-dithianaphthalenyl, 1,4-dithianaphthalenyl, etc.), benzothiophenyl or S,S-dioxide thereof (e.g. benzo[a] thiophenyl or S,S-dioxide thereof, benzo[b]thiophenyl or S,S-dioxide thereof, etc.), or the like;
- 3- to 8-membered, preferably 5- or 6-membered unsaturated hetero monocyclic group having 1 to 4 nitrogen atoms, such as pyrrolyl, pyrrolinyl, imidazolyl, pyrazolyl, pyridyl and its N-oxide, pyrimidyl, pyrazinyl, pyridazinyl, triazolyl (e.g. 4H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), dihydrotriazinyl (e.g. 4,5-dihydro-1,2,4-triazinyl, 2,5-dihydro-1,2,4-triazinyl, etc.), or the like;
- 3- to 8-membered, preferably 5- or 6-membered saturated hetero monocyclic group having 1 to 4 nitrogen atoms, such as azetydinyl, pyrrolidinyl, imidazolydinyl, piperidinyl, pyrazolydinyl, piperadinyl, or the like;
- 7- to 12-membered, preferably 9- or 10-membered unsaturated condensed heterocyclic group (preferably bicyclic group) having 1 to 2 oxygen atoms and 1 to 3 nitrogen atoms, such as benzoxazolyl, benzoxadiazolyl, or the like;
- 3- to 8-membered, preferably 5- or 6-membered unsaturated hetero monocyclic group having 1 to 2 oxygen atoms and 1 to 3 nitrogen atoms, such as oxazolyl, isooxazolyl, oxadiazolyl (e.g. 1,2,4-oxadiazolyl, 1,3,4-oxadiazolyl, 1,2,5-oxadiazolyl, etc.), or the like;
- 3- to 8-membered, preferably 5- or 6-membered saturated hetero monocyclic group having 1 to 2 oxygen atoms and 1 to 3 nitrogen atoms, such as morpholinyl or the like;
- 7- to 12-membered, preferably 9- or 10-membered unsaturated condensed heterocyclic group (preferably bicyclic group) having 1 to 2 sulfur atoms and 1 to 3 nitrogen atoms, such as benzothiazolyl, benzothiadiazolyl, or the like;
- 3- to 8-membered, preferably 5- or 6-membered unsaturated hetero monocyclic group having 1 to 2 sulfur atoms and 1 to 3 nitrogen atoms, such as thiazolyl, 1,2-thiazolyl, thiadiazolyl (e.g., 1,2,4-thiadiazolyl, 1,3, 4-thiadiazolyl, 1,2,5-thiadiazolyl, 1,2,3-thiadiazolyl, etc.), or the like;
- 3- to 8-membered, preferably 5- or 6-membered saturated hetero monocyclic group having 1 to 2 sulfur atoms and 1 to 3 nitrogen atoms, such as thiazolydinyl, or the like;
- 3- to 8-membered, preferably 5- or 6-membered unsaturated hetero monocyclic group having one sulfur atom, such as thienyl, or the like.

Suitable "esterified carboxyl groups" are exemplified below.

The suitable ester portion of the esterified carboxyl group includes a lower alkyl ester (e.g., methyl ester, ethyl ester, propyl ester, isopropyl ester, butyl ester, isobutyl ester, tertiary butyl ester, pentyl ester, hexyl ester, etc.), which may have at least one appropriate substituent. Examples of the substituted lower alkyl ester includes a lower alkanoyloxy (lower)alkyl ester (e.g., acetoxymethyl ester, propionyloxymethyl ester, butyryloxymethyl ester, valeryloxymethyl ester, pivaloyloxymethyl ester, hexanoyloxy methyl ester, 1-(or 2-)acetoxyethyl ester, 1-(2-, or 3-)acetoxypropyl ester, 1-(2-, 3- or 4-)acetoxybutyl ester, 1-(or 2-)propionyloxyethyl ester, 1-(2-, or 3-)propionyloxypropyl ester, 1-(or 2-)butyryloxyethyl ester, 1(or 2-)isobutyryloxyethyl ester, 1-(or 2-)pivaloyloxyethyl ester, 1-(or 2-)hexanoyloxyethyl ester, isobutyryloxymethyl ester, 2-ethylbutyryloxymethyl ester, 3,3-dimethylbutyryloxymethyl ester, 1-(or 2-)pentanoyloxyethyl ester, etc.), a lower alkanesulfonyl(lower)alkyl ester (e.g., 2-mesylethyl ester, etc.), a mono(di or tri)halo(lower)alkyl ester (e.g., 2-iodoethyl ester, 2,2,2-trichloroethyl ester, etc.), a lower alkoxycarbonyloxy(lower)alkyl ester (e.g., methoxycarbonyloxymethyl ester, ethoxycarbonyloxymethyl ester, propoxycarbonyloxymethyl ester, tertiary-butoxycarbonyloxymethyl ester, 1-(or 2-)methoxycarbonyloxyethyl ester, 1-(or 2-)ethoxycarbonyloxyethyl ester, or 1-(or 2-)isopropoxycarbonyloxyethyl ester, etc.), a phthalizilidene (lower)alkyl ester, and a (5-lower alkyl-2-oxo-1,3-dioxol-4-yl)(lower)alkyl ester (e.g., (5-methyl-2-oxo-1,3-dioxol-4-yl) methyl ester, (5-ethyl-2-oxo-1,3-dioxol-4-yl)methyl ester, (5-propyl-2-oxo-1,3-dioxol-4-yl)ethyl ester, etc.). Other examples of the ester portion include a lower alkenyl ester (e.g., vinyl ester, allyl ester, etc.); a lower alkynyl ester (e.g., ethynyl ester, propinyl ester, etc.); an ar(lower)alkyl ester which may have at least one appropriate substituent (e.g., benzyl ester, 4-methoxybenzyl ester, 4-nitrobenzyl ester, phenethyl ester, trityl ester, benzhydryl ester, bis (methoxyphenyl)methyl ester, 3,4-dimethoxybenzyl ester, 4-hydroxy-3,5-di-tertiary-butylbenzyl ester, etc.); an aromatic ester which may have at least one appropriate substituent (e.g., phenyl ester, 4-chlorophenyl ester, tolyl ester, tertiary-butylphenyl ester, xylyl ester, mesityl ester, cumenyl ester, etc.); a phthalidyl ester; etc.

Preferable examples of the carboxyl group protected by esterification include lower alkoxycarbonyl and phenyl(or nitrophenyl) ($C_1$–$C_4$)alkoxycarbonyl. Methoxycarbonyl, ethoxycarbonyl, and benzyloxycarbonyl are most preferred.

Suitable amidated carboxyl groups include the following:

a carbamoyl group;

a mono- or di-lower alkyl carbamoyl group (examples of the lower alkyl group are described above) (e.g., methylcarbamoyl, dimethylcarbamoyl, isopropylcarbamoyl, n-butylcarbamoyl, t-butylcarbamoyl, N-methyl-N-(pyridylmethyl) carbamoyl, etc.);

an aryl(lower alkyl)carbamoyl group (examples of the aryl group and the lower alkyl group are described above) (e.g., benzylcarbamoyl, 3,4-methylenedioxybenzylcarbamoyl, diaminobenzylcarbamoyl, phenethylcarbamoyl, etc.);

a cyclo(lower alkyl)carbamoyl group having 3 to 7 carbon atoms (examples of the cyclo lower alkyl group are described above) (e.g., cyclopropylcarbamoyl, cyclobutylcarbamoyl, cyclopentylcarbamoyl, cyclohexylcarbamoyl, etc.);

an arylcarbamoyl group (examples of the aryl group are described above) (e.g., phenylcarbamoyl, naphthylcarbamoyl, etc.);

a heterocyclic carbamoyl group (examples of the heterocyclic group are described above) (e.g., thiazolylcarbamoyl, thiadiazolylcarbamoyl, pyridylcarbamoyl, triazolylcarbamoyl, tetrazolylcarbamoyl, N-methyl-N-pyridinecarbamoyl, morpholinocarbamoyl, etc.);

a heterocyclic (lower alkyl) carbamoyl group (examples of the heterocyclic lower alkyl group are described above) (e.g., morpholinoethylcarbamoyl, pyridylmethylcarbamoyl, methylenedioxybenzylcarbamoyl, etc.);

an N-di-substituted carbamoyl group which contains a nitrogen atom as a member of a nitrogen-containing heterocyclic ring (e.g., morpholinocarbonyl, thiomorpholinocarbonyl, 1-perhydroazepinylcarbonyl, 1,1-dioxothiazolydinecarbonyl, piperidinocarbonyl, 1-piperazinylcarbonyl, 4-(2-hydroxyethyl)-1-piperazinylcarbonyl, 4-methyl-1-piperazinylcarbonyl, carboxypyrrolidinocarbonyl, etc.); a substituted sulfonylcarbomoyl group; etc.

The substituent of the substituted sulfonylcarbamoyl group includes the above-described groups such as the alkyl group having carbon atoms up to 20, the alkenyl group, the halo lower alkyl group, the aryl lower alkyl group, the hydroxy-lower alkyl group, the tri(lower alkyl)silyl(lower alkyl) group, the lower alkoxy-lower alkyl group, the lower alkylthio-lower alkyl group, the heterocyclic group, the aryl group, and the like. The aryl group may be substituted with the above-described halogen atom, the lower alkyl group, the halo lower alkyl group, the lower alkoxy group, the nitro group, or the like. Specific examples of the substituted sulfonylcarbamoyl group include naphthalenesulfonylcarbamoyl, benzenesulfonylcarbamoyl, nitrobenzenesulfonylcarbamoyl, trihalobenzenesulfonylcarbamoyl, lower alkoxybenzenesulfonylcarbamoyl, halobenzenesulfonylcarbamoyl, mono- or di-(lower alkyl)benzenesulfonylcarbamoyl, alkanesulfonylcarbamoyl having 1 to 20 carbon atoms (e.g., 2,2-dimethylethanesulfonylcarbamoyl, butanesulfonylcarbamoyl, propanesulfonylcarbamoyl, isopropanesulfonylcarbamoyl, ethanesulfonylcarbamoyl, methanesulfonylcarbamoyl, octanesulfonylcarbamoyl, pentanesulfonylcarbamoyl, isopentanesulfonylcarbamoyl, hexanesulfonylcarbamoyl, etc.), trihalo(lower) alkanesulfonylcarbamoyl (e.g., trifluoromethanesulfonylcarbamoyl, etc.), phenyl(lower) alkanesulfonylcarbamoyl, tri(lower)alkanesulfonylcarbamoyl, lower alkylthio(lower) alkanesulfonylcarbamoyl, lower alkoxy(lower) alkanesulfonylcarbamoyl, quinolinesulfonylcarbamoyl, hydroxy(lower)alkanesulfonylcarbamoyl (e.g., 2-hydroxybutanesulfonylcarbamoyl, 3-hydroxybutanesulfonylcarbamoyl, 2-hydroxypentanesulfonylcarbamoyl, etc.), alkenesulfonylcarbamoyl (e.g., ethenesulfonycarbamoyl, 1-pentenesulfonylcarbamoyl, etc.), and heterocyclic sulfonylcarbamoyl (e.g., 2-thiophenesulfonylcarbamoyl, 8-quinolinesufonylcarbamoyl, etc.).

The acylamino group means an amino group bonded to an acyl group. Preferred examples of the acyl moiety include an aliphatic acyl group, an aromatic acyl group, a heterocyclic acyl group, and an aliphatic acyl group substituted with an aromatic group or a heterocyclic group. These are derived from an acid such as carboxylic acid, carbonic acid, sulfonic acid carbamic acid, etc.

Examples of this aliphatic acyl include a saturated or unsaturated, cyclic or non-cyclic aliphatic acyl group, including alkanoyl including lower alkanoyl (e.g., formyl, acetyl, propionyl, butyryl, isobutyryl, valeryl, isovaleryl pivaloyl, hexanoyl, etc.); alkanesufonyl including lower alkanesulfonyl (e.g., mesyl, ethanesufonyl, propanesulfonyl, isopropanesulfonyl, butanesulfonyl, isobutanesulfonyl, n-pentanesulfonyl, hexanesulfonyl, etc.); carbamoyl; N-alkylcarbamoyl (e.g., methylcarbamoyl, ethylcarbamoyl, etc.); alkoxycarbonyl including lower alkoxycarbonyl (e.g., methoxycarbonyl, ethoxycarbonyl, propoxycarbonyl, butoxycarbonyl, tertiary butoxycarbonyl, etc.); alkenyloxycarbonyl including lower alkenyloxycarbonyl (e.g., vinyloxycarbonyl, allyloxycarbonyl, etc.); alkenoyl including lower alkenoyl (e.g., acryloyl, methacryloyl, crotonoyl, etc.); cycloloalkanecarbonyl including cyclo(lower)alkanecarbonyl (e.g., cyclopropanecarbonyl, cyclopentanecarbonyl, cyclohexanecarbonyl, etc.).

Examples of the aromatic acyl include $C_6$–$C_{10}$aroyl (e.g. benzoyl, toluoyl, xyloyl, etc.), N-($C_6$–$C_{10}$)aromaticcarbamoyl (e.g., N-phenylcarbamoyl, N-tolylcarbamoyl, N-naphthylcarbamoyl, etc.), $C_6$–$C_{10}$arenesulfonyl (e.g., benzenesulfonyl, tosyl, etc.), and the like.

Examples of the heterocyclic acyl include heterocyclic carbonyl, heterocyclic(lower)alkanoyl (e.g., heterocyclic acetyl, heterocyclic propanoyl, heterocyclic butanoyl, heterocyclic pentanoyl, heterocyclic hexanoyl, etc.), heterocyclic(lower)alkenoyl (e.g., heterocyclic propenoyl, heterocyclic butenoyl, heterocyclic pentenoyl, heterocyclic hexenoyl, etc.), heterocyclic glyoxyloyl, heterocyclic sulfinyl, heterocyclic sulfonyl, etc.

The aliphatic acyl substituted with aromatic groups includes aralkoxycarbonyl such as phenyl(lower)alkoxycarbonyl (e.g., benzyloxycarbonyl, phenethyloxycarbonyl, etc.).

These acyl groups may be substituted with one or more appropriate substituents, such as a nitro group. An example of preferable acyl is nitroaralkoxycarbonyl (e.g., nitrobenzyloxycarbonyl, etc.).

Preferred salts of the aromatic ring derivatives of the present invention are non-toxic, usually used pharmaceutically acceptable salts. Examples thereof include salts with inorganic bases such as salts with alkaline metals (e.g., sodium, potassium), alkaline earth metals (e.g., calcium, magnesium), ammonium, etc.; salts with organic amines (e.g., triethylamine, pyridine, picoline, ethanolamine, triethanolamine, dicyclohexylamine, N,N'-dibenzylethylenediamine, etc.); salts with inorganic acids (e.g., hydrochloric acid, hydrobromic acid, sulfuric acid, phosphoric acid, etc.); salts with organic carboxylic acids (e.g., formic acid, acetic acid, trifluoroacetic acid, maleic acid, tartaric acid, etc.); salts with sulfonic acids (e.g., methanesulfonic acid, benzenesulfonic acid, p-toluenesulfonic acid, etc.); salts with bases as well as acid-addition salts with basic or acidic amino acids (e.g., arginine, aspartic acid, glutamic acid, etc.); etc.

The compounds of the present invention can contain one or more chiral centers and can thus be enantiomers or diastereomers Some of the compounds containing the alkenyl group can be cis- or trans- isomers. In both cases, the respective isomers and their mixtures are within the scope of this invention.

The compounds of the present invention can also exist as tautomers, and individual of such tautmers and the mixture thereof are within the scope of this invention.

The compounds of the present invention and their salts can be solvates, which are also within the invention. A preferable solvent for the solvates is water or ethanol.

Specific examples of the aromatic ring derivatives of formula (III) include N-(n-pentanesulfonyl)-4-amino-3-(2,4-dichlorobenzylamino)benzamide, 4-amino-3-(N-methyl-2,4-dichlorobenzylamino)-(N-(n-pentanesulfonyl))benzamide, 4-(acetylamino)-3-((N-methyl)-2,4-dichlorobenzylamino)-(N-(n-pentanesulfonyl))benzamide, etc.

Specific examples of the aromatic ring derivatives of formula (IV) include (E)-N-(n-pentanesulfonyl)-2-(4-phenylphenyl)ethenylpyridine-4-carboxyamide, etc.

Specific examples of the aromatic ring derivatives of formula (V) include (E)-3-(4-bromo-1-(2,4-dichlorobenzyl)-2-methylimidazol-5-yl)-N-(n-pentanesulfonyl)-2-propenamide, (E)-3-(1-(2,4-dichlorobenzyl)-2-methyl-imidazol-5-yl)-N-(n-pentanesulfonyl)-2-propenamide, (E)-3-(4-chloro-1-(2,4-dichlorobenzyl)-2-methylimidazol-5-yl)-N-(n-pentanesulfonyl)-2-propenamide, (E)-3-(4-chloro-1-(2,4-dichlorobenzyl)-2-methylimidazol-5-yl)-N-benzenesulfonyl-2-propenamide, (E)-3-(1-(2,4-dichlorobenzyl)-2-methyl-4-phenylimidazol-5-yl)-N-(n-pentanesulfonyl)-2-propenamide, (E)-3-(1-(2,4-dichlorobenzyl)-2-methyl-4-phenylimidazol-5-yl)-N-benzenesulfonyl-2-propenamide, (E)-3-(1-(2,4-dichlorobenzyl)-2-methylimidazol-4-yl))-N-(n-pentanesulfonyl)-2-propenamide, (E)-3-(1-(2,4-dichlorobenzyl)-2-methylimidazol-5-yl)-N-(n-pentanesulfonyl)-2-((thiophen-2-yl)methyl)-2-propenamide, (E)-2-benzyl-3-(1-(2,4-dichlorobenzyl)-2-methylimidazol-5yl)-N-(n-pentanesulfonyl)-2-propenamide, etc.

Specific examples of the aromatic ring derivatives of formula (VI) include 3-(1-(2,4-dichlorobenzyl)-2-methylimidazol-5-yl)-N-(n-pentanesulfonyl) propionamide, (E)-3-(1-(2,4-dichlorobenzyl)-2-methylimidazol-4-yl))-N-(n-pentanesulfonyl) propionamide, etc.

The aromatic ring derivatives and their pharmaceutically acceptable salts of the present invention are effective for preventing and treating various disorders such as impaired glucose tolerance, diabetes (type II diabetes), diabetic complications (e.g., diabetic gangrene, diabetic arthropathy, diabetic osteopenia, diabetic glomerulosclerosis, diabetic nephropathy, diabetic dermatopathy, diabetic neuropathy, diabetic cataract, diabetic retinopathy, etc.), syndrome of insulin resistance (e.g., insulin receptor disorders, Rabson-Mendenhall syndrome, leprechaunism, Kobberling-Dunnigan syndrome, Seip syndrome, Lawrence syndrome, Cushing syndrome, acromegaly, etc.), polycystic ovary syndrome, hyperlipidemia, atherosclerosis, cardiovascular disorders (e.g., stenocardia, cardiac failure, etc.), hyperglycemia (e.g., those characterized by abnormal saccharometabolism such as feeding disorders, etc.), and hypertension, based on their blood sugar level-depressing activity; stenocardia, hypertension, pulmonary hypertension, congestive heart failure, glomerulopathy (e.g., diabetic glomerulosclerosis, etc.), tubulointerstitial disorders (e.g., renopathy induced by FK506, cyclosporin, etc.), renal failure, atherosclerosis, angiostenosis (e.g., after percutaneous arterioplasty), distal angiopathy, cerebral apoplexy, chronic reversible obstructions (e.g., bronchitis, asthma (chronic asthma, allergic asthma), etc.), autoimmune diseases, allergic rhinitis, urticaria, glaucoma, diseases characterized by enteromotility disorders (e.g., hypersensitive enteropathy syndrome, etc.), impotence (e.g., organic impotence, psychic impotence, etc.), and diabetic complications (e.g., diabetic gangrene, diabetic arthropathy, diabetic osteopenia, diabetic glomerulosclerosis, diabetic nephropathy, diabetic dermatopathy, diabetic neuropathy, diabetic cataract, diabetic retinopathy, etc.), nephritis, cachexia (e.g., progressive weight loss due to lipolysis, myolysis, anemia, edema, anorexia etc., in chronic diseases including cancer, tuberculosis, endocrinopathy, AIDS, etc.), pancreatitis, and restenosis after PTCA, based on their cGMP-PDE (especially PDE-V)-inhibiting activity, smooth muscle relaxing activity, bronchodilating activity, vasodilating activity, smooth muscle cell suppressing activity, anti-allergic activity, and the like.

The aromatic ring derivatives of the present invention can be formulated into conventional dosage forms for pharmaceutical compositions as an active ingredient together with pharmaceutically acceptable carriers, such as organic or inorganic solid or liquid vehicles, suitable for oral administration, parenteral administration or external application to be used for treating diseases or disorders as described above. The pharmaceutical compositions can be of any solid form such as tablets, granules, powders, capsules, etc., or of any liquid form such as solutions, suspensions, syrups, emulsions, lemonades, etc.

If desired, the pharmaceutical compositions can further contain an auxiliary, a stabilizer, a wetting agent, and other usually used additives such as lactose, citric acid, tartaric acid, stearic acid, magnesium stearate, terra alba, sucrose, corn starch, talc, gelatin, agar, pectin, peanut oil, olive oil, cacao butter, ethylene glycol, etc.

The dose of the derivative of the present may vary depending on the age and the condition of patients, the type and the condition of diseases, and the type of the derivative to be used. In general, the derivative is administered to a patient at a dose of from 1 to 100 mg/kg for oral administration and from 0.1 to 10 mg/kg for intramuscular injection or intravenous injection, once to four times a day.

BEST MODE FOR CARRYING OUT THE INVENTION

Production Example 1

Production of N-(n-pentanesulfonyl)-3-(acetylamino)-4-nitrobenzamide

Figure 1:
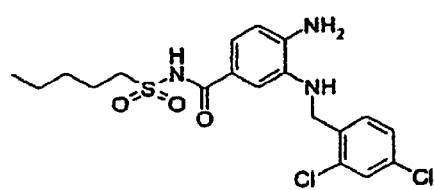
FIG. 1 shows chemical formulae of compounds (31) to (36).
Figure 1:
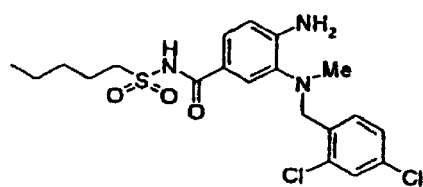
Figure 1:
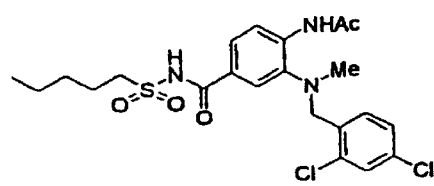
Figure 1:
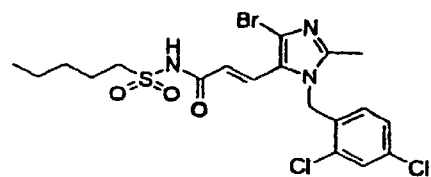
Figure 1:
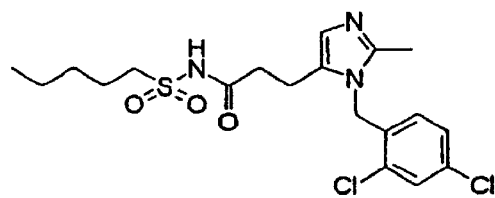
Figure 1:
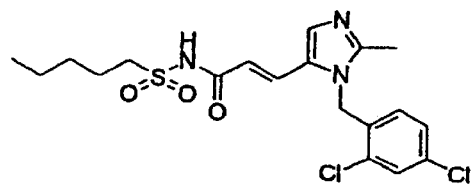
Figure 2:
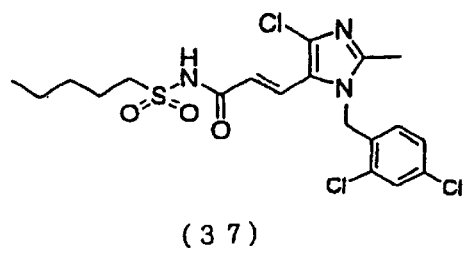
FIG. 2 shows chemical formulae of compounds (37) to (43).
Figure 2:
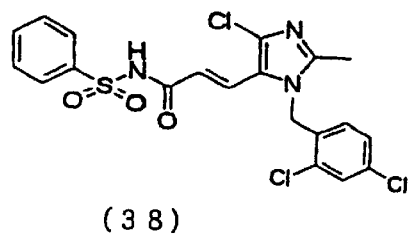
Figure 2:
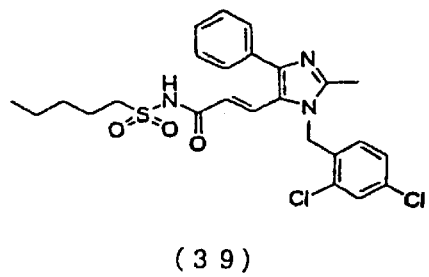
Figure 2:
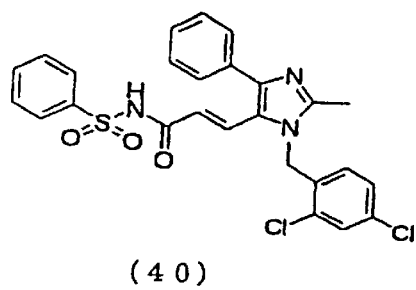
Figure 2:
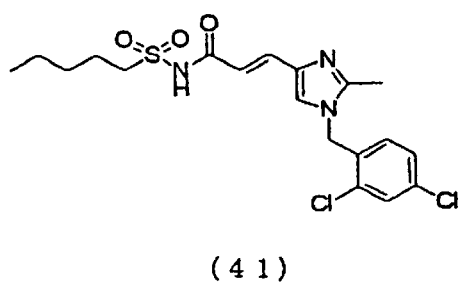
Figure 2:
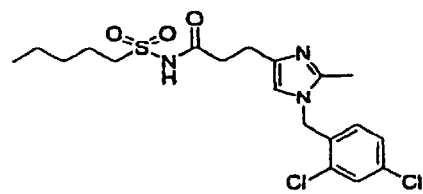
Figure 2:
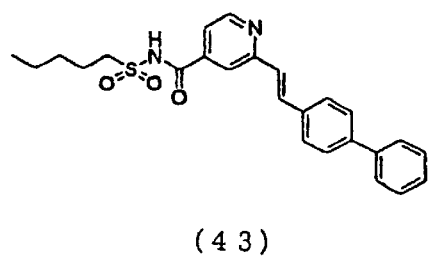
Figure 3:
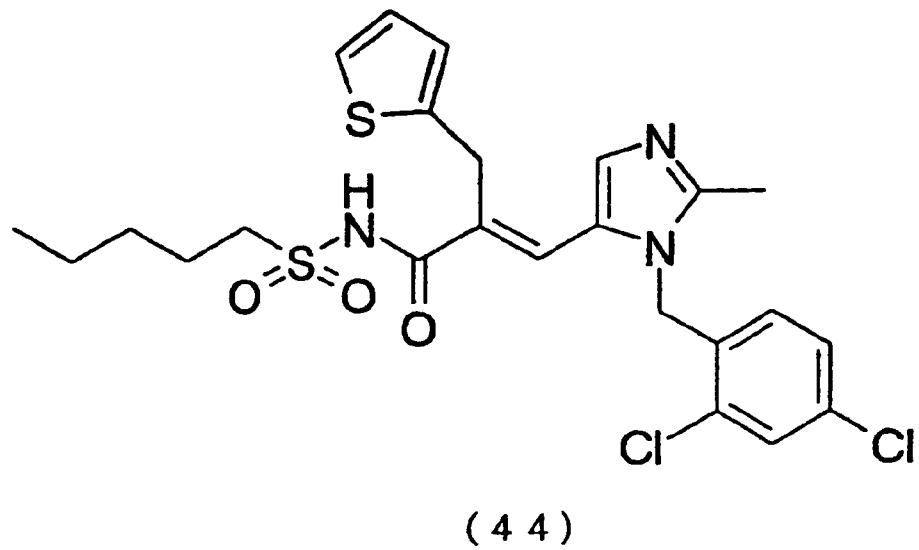
FIG. 3 shows chemical formulae of compounds (44) and (45).
Figure 3:
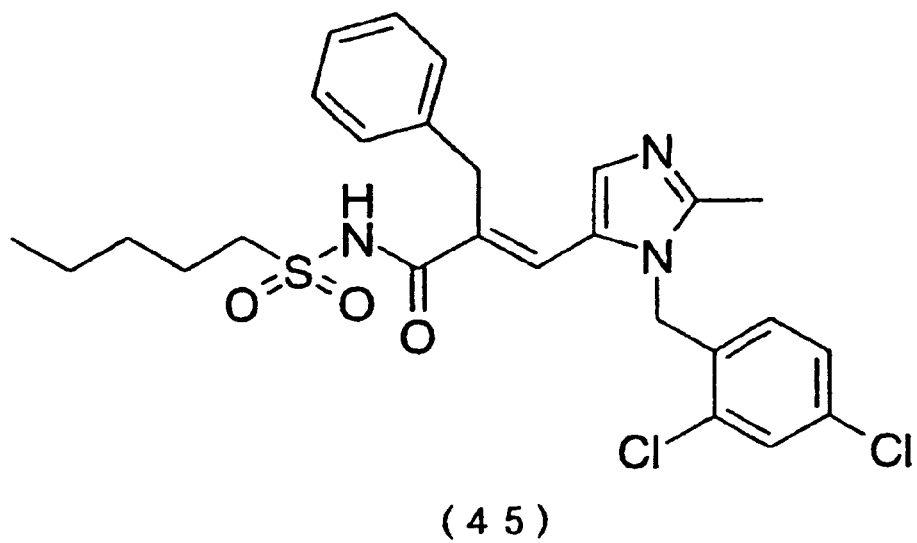

N,N'-carbonyldiimidazole (65.09 g) was added all at once to a solution (200 ml) of N,N-dimethylformamide containing 3-acetylamino-4-nitrobenzoic acid (60.22 g), and the reaction mixture was stirred at room temperature for 1 hour. 1-pentanesulfonamide (60.72 g) and 1,8-diazabicyclo[5.4.0]undec-7-ene (61.12 g) were added thereto, and the mixture was stirred at 100° C. for 16 hours. The solvent was evaporated at 90° C. under reduced pressure using a vacuum pump. Chloroform and water were added to the resulting residue, and the pH of the aqueous layer was adjusted to 4 with diluted hydrochloric acid with stirring. The organic layer was separated, dried over sodium sulfate, and then concentrated to yield partially purified N-(n-pentanesulfonyl)-3-(acetylamino)-4-nitrobenzamide. The product was used immediately in the next reaction step.

Production Example 2

Production of N-(n-pentanesulfonyl)-3-amino-4-nitrobenzamide

The above partially purified product of N-(n-pentanesulfonyl)-3-(acetylamino)-4-nitrobenzamide was mixed with 300 ml of water and 500 ml of ethanol. Two-hundred grams of a 10%-sodium hydroxide aqueous solution were added thereto, and the mixture was stirred at 45 to 50° C. for 6 hours. The solvent (approx. 300 ml) was evaporated under reduced pressure. The resulting residue was neutralized with 10% hydrochloric acid aqueous solution and adjusted to pH 2 with diluted hydrochloric acid. The precipitated crystals were collected by filtration and dried to give 85.0 g of yellow crystals of N-(n-pentanesulfonyl)-3-amino-4-nitrobenzamide.

Properties of the compound:
$^1$H-NMR (DMSO-d6, δ ppm): 0.84(3H, t, J=7.5 Hz), 1.27(2H, m), 1.36(2H, m), 1.68(2H, m), 3.48(2H, t, J=6.0 Hz), 6.99(1H, dd, J=1.5 and 9.0 Hz), 7.40–7.60(2H, brs), 7.50(1H, d, J=1.5 Hz), 8.03(1H, d, J=9.0 Hz), 12.0–13.0(1H, brs).

Production Example 3

Production of N-(n-pentanesulfonyl)-3-(2,4 dichlorobenzylamino)-4-nitrobenzamide N-(n-pentanesulfonyl)-3-amino-4-nitrobenzamide (85.0 g) was mixed with 2,4-dichlorobenzyl chloride (105.4 g), sodium iodide (20.0 g), potassium carbonate (113.3 g), and methanol (120 ml). The mixture was stirred at 60° C. for 24 hours. After 105.4 g of 2,4-dichlorobenzyl chloride was added, the mixture was stirred at 60° C. for another 24 hour. Another 105.4 g of 2,4-dichlorobenzyl chloride was added, and the mixture was continued to be stirred at 60° C. for 30 hours. The mixture was then cooled down, and 500 ml of ethyl acetate and 500 ml of a saturated sodium hydrogen aqueous solution with carbonate were added to the mixture. The mixed solution was stirred, and the resulting crystals precipitated were filtrated. The filtrate was separated into aqueous and organic layers, and the organic layer was concentrated to yield crystals. All the crystals were combined together, and washed with water and ethyl acetate to give 66.6 g of orange crystals of N-(n-pentanesulfonyl)-3-(2,4-dichlorobenzylamino)-4-nitrobenzamide.

Properties of the compound:
$^1$H-NMR (DMSO-d6, δ ppm): 0.84(3H, t, J=7.5 Hz), 1.15–1.30(4H, m), 1.40–1.60(2H, m), 2.94(2H, t, J=7.5 Hz), 4.66 (2H, d, J=6.0 Hz), 7.22(1H, dd, J=1.5 and 8.5 Hz), 7.27(1H, d, J=1.5 Hz), 7.30(1H, d, J=8.5 Hz), 7.37(1H, dd, J=2.0 and 8.5 Hz), 7.65(1H, d, J=2.0 Hz), 8.04(1H, d, J=8.5 Hz), 8.58(1H, t, J=6.0 Hz), 11.32(1H, brs).

EXAMPLE 1

Synthesis of N-(n-pentanesulfonyl)-4-amino-3-(2,4-dichlorobenzylamino)benzamide (31)

N-(n-pentanesulfonyl)-3-(2,4-dichlorobenzylamino)-4-nitrobenzamide (38.9 g) was mixed with 200 ml of tetrahydrofuran, 200 ml of ethanol and 800 ml of water. Sodium hydrosulfite (214.2 g) was added all at once to the mixture with stirring. Immediately, the mixture was placed on an oil bath at 90° C. and refluxed for 40 minutes. The mixture was then cooled down and separated into aqueous and organic layers. The organic layer was concentrated, and water was added to the resulting residue. The precipitate thus formed was separated by filtration, and washed subsequently with water and ethyl acetate. Ethanol (520 ml) was added to the resulting solid, and the mixture was refluxed at 100° C. to dissolve the solid completely. Water (230 ml) was added to the heated solution, and the mixture was cooled with stirring for 1 hour. The resulting crystals were separated through filtration, washed with a solution of ethanol/water (7:3) and dried to give pale-yellow crystals (19.9 g) of N-(n-pentanesulfonyl)-4-amino-3-(2,4-dichlorobenzylamino)benzamide (31).

Properties of compound (31):
$^1$H-NMR(DMSO-d6, δ ppm): 0.81(3H, t, J=7.3 Hz), 1.24(2H, m), 1.32(2H, m), 1.62(2H, m), 3.40(2H, m), 4.38 (2H, d, J=5.8 Hz), 5.32(1H, t, J=5.8 Hz), 5.59(2H, brs), 6.56(1H, d, J=8.2 Hz), 6.85(1H, d, J=1.8 Hz), 7.20(1H, dd, J=8.2 and 1.8 Hz), 7.36(1H, d, J=8.5 Hz), 7.39(1H, dd, J=8.5 and 2.1 Hz), 7.63(1H, d, J=1.8 Hz), 11.32(1H, brs).
IR(Nujol): 1661 cm$^{-1}$.
mp: 180–182° C.

Production Example 4

Production of 3-(N-methyl-2,4-dichlorobenzylamino)-4-nitrobenzoic acid

A solution of 10 ml N,N-dimethylformamide containing 3-fluoro-4-nitrobenzoic acid (1.00 g), N-methyl-2,4-dichlorobenzylamine (1.54 g) and sodium carbonate (1.15 g) was stirred at 100° C. for 14 hours. The reaction mixture was extracted using water and ethyl acetate with stirring. The organic layer was separated and concentrated, and then methanol was added to the resulting residue. After removal of an insoluble material, the solvent was evaporated. The resulting residue was purified by silica-gel column chromatography to give 0.85 g of 3-(N-methyl-2,4-dichlorobenzylamino)-4-nitrobenzoic acid.
Properties of the compound:
$^1$H-NMR(DMSO-d6, δ ppm): 2.75(3H, s), 4.42(2H, s), 7.39(1H, d, J=8.4 Hz), 7.43(1H, dd, J=8.4 and 2.0 Hz), 7.46(1H, dd, J=8.4 and 1.4 Hz), 7.63(1H, d, J=2.0 Hz), 7.68(1H, d, J=1.4 Hz), 7.77(1H, d, J=8.4 Hz).

Production Example 5

Production of N-(n-pentanesulfonyl)-3-(N-methy-2,4-dichlorobenzylamino)-4-nitrobenzamide N,N'-carbonyldiimidazole (0.776 g) was added to a mixture of 0.85 g of 3-(N-methyl-2,4-dichlorobenzylamino)-4-nitrobenzoic acid and 10 ml N,N-dimethylformamide at room temperature, and the mixture was stirred for 1 hour. 1-Pentanesulfonamide (0.724 g) and 1,8-diazabicyclo[5.4.0]undec-7-ene (0.729 g) were then added thereto, and the resulting mixture was stirred at 100° C. for 21 hours. The mixture was concentrated, and the resulting residue was dissolved in ethyl acetate. The organic layer was washed with water, concentrated, and purified by silica-gel column chromatography (eluent: a mixture of hexane and ethyl acetate at a ratio of 1:1 to 0:1). The desired fractions were collected and concentrated. The concentrate was re-dissolved in ethyl acetate, washed twice with diluted hydrochloric acid and subsequently with a solution of sodium hydrogen carbonate. The organic layer was dried and concentrated to give 0.605 g of N-(n-pentanesulfonyl)-3-(N-methy-2,4-dichlorobenzylamino)-4-nitrobenzamide. This product was used immediately in the next reaction step.

EXAMPLE 2

Synthesis of 4-amino-3-(N-methyl-2,4-dichlorobenzylamino)-(N-(n-pentanesulfonyl))benzamide (32)

Four milliliters of ethanol and 4 ml of tetrahydrofuran were added to 0.605 g of N-(n-pentanesulfonyl)-3-(N-methy-2,4-dichlorobenzylamino)-4-nitrobenzamide, and subsequently 10 ml of an aqueous solution containing 3.10 g of sodium hydrosulfite was added thereto. The mixture was stirred at 80° C. for 20 minutes and then extracted with water and ethyl acetate. The organic layer was washed with water and concentrated. The resulting residue was crystallized from ether, filtrated, and dried to obtain 0.126 g of 4-amino-3-(N-methyl-2,4-dichlorobenzylamino)-(N-(n-pentanesulfonyl))benzamide (32).

Properties of compound (32):
$^1$H-NMR(DMSO-d6, δ ppm): 0.84(3H, t, J=7.2 Hz), 1.34–1.42(2H, m), 1.42–1.48(2H, m), 1.63–1.70(2H, m), 2.51(3H, s), 3.46(2H, t, J=7.8 Hz), 4.12(2H, s), 5.79(2H, s), 6.68(1H, d, J=8.6 Hz), 7.37(1H, dd, J=8.2 and 2.0 Hz),7.50 (1H, dd, J=8.4 and 1.9 Hz), 7.55(1H, d, J=8.4 Hz), 7.58(1H, d, J=2.2 Hz), 7.67(1H, d, J=1.9 Hz), 11.48(1H, s).
IR(Nujol): 1651 cm$^{-1}$.
Mass(FD): m/e 457(M).
mp: 122.5–124° C.

EXAMPLE 3

Synthesis of 4-(acetylamino)-3-((N-methyl)-2,4-dichlorobenzylamino)-(N-(n-pentanesulfonyl))benzamide (33)

4-amino-3-((N-methyl)-2,4-dichlorobenzylamino)-(N-(n-pentanesulfonyl))benzamide was dissolved in chloroform, and triethylamine and acetyl chloride were added to the solution. The reaction mixture was stirred at room temperature for 30 minutes. The reaction solution was mixed with water and separated into aqueous and organic layers. The organic layer was washed with water and concentrated. The resulting residue was crystallized from ether. The crystals were filtrated and dried to yield 4-(acetylamino)-3-((N-methyl)-2,4-dichlorobenzylamino)-(N-(n-pentanesulfonyl))benzamide (33).
Properties of compound (33):
$^1$H-NMR(DMSO-d6, δ ppm): 0.84(3H, t, J=7.3 Hz), 1.25–1.32(2H, m), 1.34–1.42(2H, m), 1.65–1.73(2H, m), 2.08(3H, s), 2.64(3H, s), 3.51(2H, t, J=7.7 Hz), 4.14(2H, s), 7.37(1H, dd, J=8.3 and 2.2 Hz), 7.47(1H, d, J=8.3 Hz), 7.61(1H, d, J=2.1 Hz), 7.68(1H, dd, J=8.5 and 1.9 Hz), 7.90(1H, d, J=1.9 Hz),8.11(1H, d, J=8.6 Hz), 9.14(1H, s), 11.95(1H, s).
IR(Nujol): 1662 cm$^{-1}$.
Mass(FD): m/e 499(M).
mp: 163.5–165° C.

Production Example 6

Production of 4,5-dibromo-2-methyl-1-(2-(trimethylsilyl)ethoxymethyl)immidazole

A 901 mg portion of 60% sodium hydride was added little by little to ice-cold N,N-dimethylformamide (50 ml) containing 4.91 g of 4,5-dibromo-2-methylimidazole. The reaction mixture was stirred at room temperature for 1 hour. 2-(Trimethysilyl)ethoxymethyl chloride (3.75 g) was added dropwise to the mixture on ice, and the mixture was stirred at room temperature overnight. The solvent was evaporated under reduced pressure, ethyl acetate was added to the resulting residue, and the mixture was washed subsequently with a saturated sodium hydrogen carbonate aqueous solution and a sodium chloride aqueous solution. The organic layer was dried over anhydrous magnesium sulfate, and the solvent was evaporated under reduced pressure. The resulting residue was purified by silica-gel column chromatography (eluent, hexane:ethyl acetate=3:1) to obtain 7.6 g of colorless oily material of 4,5-dibromo-2-methyl-1-(2-(trimethylsilyl)ethoxymethyl)imidazole.
Properties of the compound:
$^1$H-NMR(CDCl$_3$): 0.00(9H, s), 0.92(2H, t, J=8 Hz), 2.47 (3H, s), 3.55(2H, t, J=8 Hz), 5.24(2H, s).

Production Example 7

Production of 4-bromo-2-methyl-1-(2-(trimethylsilyl)ethoxymethyl)imidazole-5-carboxyaldehyde A solution (58.1 ml) of 1.63N n-butyllithium in hexane was added dropwise to 250 ml of tetrahydrofuran containing 29.2 g of 4,5-dibromo-2-methyl-1-(2-(trimethylsilyl) ethoxymethyl)imidazole over a period of 20 minutes at −55° C. to −60° C. After the mixture was stirred at −60° C. for 30 minutes, N,N-dimethylformamide (58 g) was added dropwise to the mixture at −55° C. to −60° C., followed by stirring at room temperature for 1 hour. A saturated sodium chloride aqueous solution was added thereto, and the mixture was extracted with ethyl acetate. The organic layer was dried over sodium sulfate anhydride, and the solvent was evaporated under reduced pressure. The resulting residue was purified by silica-gel column chromatography (eluent, hexane:ethyl acetate=3:1) to yield 18.5 g of pale-yellow oily matetial of 4-bromo-2-methyl-1-(2-(trimethylsilyl) ethoxymethyl)imidazole-5-carboxyaldehyde.
Properties of the compound:
$^1$H-NMR(CDCl$_3$): 0.00(9H, s), 0.91(2H, t, J=8 Hz), 2.52 (3H, s), 3.58(2H, t, J=8 Hz), 5.70(2H, s), 9.71(1H, s).

Production Example 8

Production of 5-bromo-2-methylimidazole-4-carboxyaldehyde

Eighty milliliters of hydrochloric acid (6N) were added to a solution of 4-bromo-2-methyl-1-(2-(trimethylsilyl) ethoxymethyl)imidazole-5-carboxyaldehyde (18.5 g) in 80 ml of ethanol, and the mixture was heated under reflux for 1 hour. The solvent was evaporated under reduced pressure, and a saturated sodium hydrogen carbonate aqueous solution was added to the residue cooled with ice until the pH of the mixture became weak alkali. The precipitated crystals were filtered, washed with methanol, and heated to dryness under reduced pressure to give 9.17 g of white crystals of 5-bromo-2-methylimidazole-4-carboxyaldehyde.
Properties of the compound:
$^1$H-NMR(CDCl$_3$): 2.45(3H, s), 9.53(1H, s).

Production Example 9

Production of 4-bromo-1-(2,4-dichlorobenzyl)-2-methylimidazole-5-carboxyaldehyde 5-bromo-2-methylimidazole-4-carboxyaldehyde (2.25 g) and potassium carbonate (2.47 g) were dissolved in 15 ml of N,N-dimethylformamide, and 1 ml of N,N-dimethylformamide containing 2.56 g of 2,4-dichlorobenzyl chloride was added thereto. The reaction mixture was stirred at room temperature overnight and then at 70° C. for 1 hour. Ethyl acetate was added to the mixture, which was washed subsequently with water and a sodium chloride aqueous solution. The organic layer was dried over anhydrous magnesium sulfate, and the solvent was evaporated under reduced pressure. The residue was purified by silica-gel column chromatography (eluent, hexane:ethyl acetate=4:1) to give 3.42 g of white crystals of 4-bromo-1-(2,4-dichlorobenzyl)-2-methylimidazole-5-carboxyaldehyde.
Properties of the compound:
$^1$H-NMR(CDCl$_3$): 2.34(3H, s), 5.58(2H, s), 6.42(1H, d, J=8 Hz), 7.16(1H, dd, J=2, 8 Hz), 7.45(1H, d, J=2 Hz), 9.70(1H, s).

Production Example 10

Production of methyl (E)-3-(4-bromo-1-(2,4-dichlorobenzyl)-2-methylimidazol-5-yl)-2-propenoate One gram of 4-bromo-1-(2,4-dichlorobenzyl)-2-methylimidazole-5-carboxyaldehyde was dissolved in 10 ml of tetrahydrofuran and then 1.01 g of methyl (triphenylphosphoranilidene)acetate was added thereto under cooling with ice. After being heated under reflux for 3 hours, 290 mg of methyl(triphenylphosphoranilidene) acetate was added to the mixture, which was further heated under reflux for another 3 hours. The solvent was evaporated under reduced pressure, and the resulting residue was purified by silica-gel column chromatography (eluent, hexane-:ethyl acetate=4:1) to obtain 1.04 g of pale-yellow crystals of methyl (E)-3-(4-bromo-1-(2,4-dichlorobenzyl)-2-methylimidazol-5-yl)-2-propenoate.
Properties of the compound:
$^1$H-NMR(CDCl$_3$): 2.36(3H, s), 3.75(3H, d, J=2 Hz), 5.20 (2H, s), 6.39(1H, d, J=8 Hz), 6.53(1H, d, J=15 Hz), 7.17(1H, dd, J=2, 8 Hz), 7.26(1H, d, J=2 Hz), 7.47(1H, d, J=2 Hz).

Production Example 11

Production of (E)-3-(4-bromo-1-(2,4-dichlorobenzyl)-2-methylimidazol-5-yl)-2-propenoic acid Methyl (E)-3-(4-bromo-1-(2,4-dichlorobenzyl)-2-methyl-imidazol-5-yl)-2-propenoate (800 mg) was dissolved in 20 ml of methanol, and then 20 ml of 1N sodium hydroxide was added to the solution. After being heated under reflux for 30 minutes, the solution was adjusted to an acidic pH with 1N hydrochloric acid under cooling with ice, and extracted with dichloromethane. The organic layer was washed with a sodium chloride aqueous solution, dried over anhydrous magnesium sulfate, and then the solvent was evaporated under reduced pressure to yield 762 mg of white crystals of (E)-3-(4-bromo-1-(2,4-dichlorobenzyl)-2-methylimidazol-5-yl)-2-propenoic acid.
Properties of the compound:
$^1$H-NMR(DMSO-d6): 2.32(3H, s), 5.39(2H, s), 6.28(1H, d, J=15 Hz), 6.51(1H, d, J=8 Hz), 7.20(1H, d, J=15 Hz), 7.39(1H, dd, J=2, 8 Hz), 7.74(1H, d, J=3 Hz).

EXAMPLE 4

Synthesis of (E)-3-(4-bromo-1-(2,4-dichlorobenzyl)-2-methylimidazol-5-yl)-N-(n-pentanesulfonyl)-2-propenamide (34)

(E)-3-(4-bromo-1-(2,4-dichlorobenzyl)-2-methylimidazol-5-yl)-2-propenoic acid (696 mg) was suspended in 7 ml of N,N-dimethylformamide, and 376 mg of N,N'-carbonyldiimidazole were added thereto. The reaction mixture was stirred at room temperature for 1 hour, and then 405 mg of pentanesulfonamide and 407 mg of 1,8-diazabicyclo[5.4.0]undec-7-ene were added thereto. The mixture was stirred at 100° C. for 3 hours, adjusted to a weak acid pH with a 1N hydrochloric acid solution under ice-cooling and then extracted with dichloromethane. The organic layer was washed with a sodium chloride aqueous solution, dried over anhydrous magnesium sulfate. The solvent was then evaporated, and the resulting residue was mixed with diisopropyl ether. The precipitated crystals were filtered and dried under reduced pressure to obtain 800 mg of white crystals of (E)-3-(4-bromo-1-(2,4-dichlorobenzyl)-2-methylimidazol-5-yl)-N-(n-pentanesulfonyl)-2-propenamide (34).
Properties of Compound (34):
$^1$H-NMR(DMSO-d6): 0.82(3H, t, J=7 Hz), 1.20–1.40(4H, m), 1.57–1.67(2H, m), 2.33(3H, s), 3.32–3.40(2H, m), 5.39 (2H, s), 6.52(1H, d, J=9 Hz), 6.69(1H, d, J=15 Hz), 7.27(1H, d, J=15 Hz), 7.38(1H, dd, J=2, 8 Hz), 7.75(1H, s).
Mass(ESI): 522(M−H).

EXAMPLE 5

Synthesis of 3-(1-(2,4-dichlorobenzyl)-2-methylimidazol-5-yl)-N-(n-pentanesulfonyl)-propionamide (35)

(E)-3-(4-bromo-1-(2,4-dichlorobenzyl)-2-methylimidazol-5-yl)-N-(n-pentanesulfonyl)-2-propenamide (630 mg) was dissolved in a mixed solvent of methanol (6 ml) and 1,4-dioxane (6 ml), and 100 mg of 10% palladium carbon and 130 mg of potassium acetate were added thereto. Catalytic reduction of the solution was carried out under a hydrogen atmosphere of 1 atm for 5 hours, and the reduction was allowed to further proceed under a hydrogen atmosphere of 3 atms for 4 hours. The catalyst was removed by filtration, and the solvent was evaporated under reduced pressure. The resulting residue was mixed with dichloromethane, and washed with water and then with a sodium chloride aqueous solution. The organic layer was dried over anhydrous magnesium sulfate, and the solvent was evaporated under reduced pressure. The residue was purified by the silica-gel column chromatography (eluent, methanol:dichloromethane=3:97) to give 290 mg of pale-yellow powder of 3-(1-(2,4-dichlorobenzyl)-2-methyl-imidazol-5-yl)-N-(n-pentanesulfonyl)-2-propionamide (35).

Properties of Compound (35):
$^1$H-NMR(DMSO-d6): 0.92(3H, t, J=8 Hz), 1.18–1.35(4H, m), 1.53–1.63(2H, m), 2.16(3H, s), 2.52–2.60(4H, m), 3.27 (2H, d, J=8 Hz), 5.17(2H, s), 6.30(1H, d, J=8 Hz), 6.64(1H, s), 7.36(1H, dd, J=2, 8 Hz), 7.72(1H, d, J=2 Hz).
Mass(ESI): m/e 444(M–H).

Production Example 12

Production of 1-(2,4-dichlorobenzyl)-2-methylimidazol-5-carboxyaldehyde 4-bromo-1-(2,4-dichlorobenzyl)-2-methylimidazol-5-carboxyaldehyde (500 mg) was dissolved in 5 ml of 1,4-dioxane, and 100 mg of 10% palladium carbon and 155 mg of potassium acetate were added thereto. Catalytic reduction of the solution was performed under a hydrogen atmosphere of 1 atm for 7 hours. The catalyst was removed by filtration, and then the solvent was evaporated under reduce pressure. Ethyl acetate was added to the resulting residue, and the mixture was washed subsequently with water and a sodium chloride aqueous solution. The organic layer was dried over anhydrous magnesium sulfate, and the solvent was evaporated to give 379 mg of white crystals of 1-(2,4-dichlorobenzyl)-2-methylimidazol-5-carboxyaldehyde.

Properties of the compound:
$^1$H-NMR(CDCl$_3$): 2.38(3H, s), 5.62(2H, s), 6.33(1H, d, J=8 Hz), 7.13(1H, d, J=8 Hz), 7.45(1H, d, J=2 Hz), 7.82(1H, s), 9.69(1H, s).

Production Example 13

Production of methyl (E)-3-(1-(2,4-dichlorobenzyl)-2-methylimidazol-5-yl)-2-propenoate Methyl (E)-3-(1-(2,4-dichlorobenzyl)-2-methylimidazol-5-yl)-2-propenoate (330 mg) was obtained as white crystals from 346 mg of 1-(2,4-dichlorobenzyl)-2-methylimidazole-5-carboxyaldehyde in the same manner as in Production Example 10.

Properties of the compound:
$^1$H-NMR(CDCl$_3$): 2.35(3H, s), 3.73(3H, s), 5.18(2H, s), 6.16(1H, d, J=15 Hz), 6.30(1H, d, J=8 Hz), 7.15(1H, dd, J=2,8 Hz), 7.26(1H, d, J=3 Hz), 7.42–7.55(1H, m), 7.65–7.70 (1H, m).

Production Example 14

Production of (E)-3-(1-(2,4-dichlorobenzyl)-2-methyl-imidazol-5-yl)-2-propenoic acid (E)-3-(1-(2,4-dichlorobenzyl)-2-methylimidazol-5-yl)-2-propenoic acid (210 mg) was obtained as white crystals from 300 mg of methyl (E)-3-(1-(2,4-dichlorobenzyl)-2-methyl-imidazol-5-yl)-2-propenoate in the same manner as in Production Example 11.

Properties of the compound:
$^1$H-NMR(DMSO-d6): 2.29(3H, s), 5.34(2H, s), 6.17(1H, d, J=15 Hz), 6.35(1H, d, J=8 Hz), 7.23(1H, d, J=15 Hz), 7.38(1H, dd, J=2, 8 Hz), 7.60(1H, s), 7.75(1H, s).

EXAMPLE 6

Synthesis of (E)-3-(1-(2,4-dichlorobenzyl)-2-methyl-imidazol-5-yl)-N-(n-pentanesulfonyl)-2-propenamide (36)

(E)-3-(1-(2,4-dichlorobenzyl)-2-methylimidazol-5-yl)-N-(n-pentanesulfonyl)-2-propenamide (36) (164 mg) was obtained as white crystals from 177 mg of (E)-3-(1-(2,4-dichlorobenzyl)-2-methylimidazol-5-yl)-2-propenoic acid in the same manner as in Example 4.

Properties of Compound (36):
$^1$H-NMR(DMSO-d6): 0.82(3H, t, J=7 Hz), 1.20–1.38(4H, m), 1.55–1.67(2H, m), 2.27(3H, s), 3.30–3.40(2H, m), 5.36 (2H, s), 6.30(1H, d, J=15 Hz), 6.36(1H, d, J=8 Hz), 7.34(1H, d, J=15 Hz), 7.38(1H, dd, J=2, 8 Hz), 7.53(1H, s), 7.73(1H. d, J=2 Hz)
Mass(ESI): m/e 444(M+H).

Production Example 15

Production of 5-chloro-2-methylimidazole-4-carboxyaldehyde 5-bromo-2-methylimidazole-4-carboxyaldehyde (400 mg) was dissolved in 6 ml of concentrated hydrochloric acid, and the solution was heated under reflux for 24 hours. A saturated sodium hydrogen carbonate aqueous solution was added to the reaction mixture under ice-cooling until the pH of the mixture became weak alkali, and the mixture was extracted twice with ethyl acetate. The organic layer was washed subsequently with a saturated sodium hydrogen carbonate aqueous solution and a sodium chloride aqueous solution. The organic layer was dried over anhydrous magnesium sulfate, and the solvent was evaporated under reduced pressure. Hexane was added to the residue, and the resulting crystals were filtered to give 222 mg of yellow crystals of 5-chloro-2-methylimidazole-4-carboxyaldehyde.Properties of the compound:
$^1$H-NMR(CDCl$_3$): 2.45(3H, s), 9.58(1H, s).

Production Example 16

Production of 4-chloro-1-(2,4-dichlorobenzyl)-2-methylimidazole-5-carboxaldehyde 4-Chloro-1-(2,4-dichlorobenzyl)-2-methylimidazole-5-carboxaldehyde (270 mg) was obtained as pale-yellow crystals from 205 mg of 5-chloro-2-methylimidazole-4-carboxaldehyde in the same manner as in Production Example 9.

Properties of the compound:
$^1$H-NMR(CDCl$_3$): 2.32(3H, s), 5.57(2H, s), 6.43(1H, d, J=8 Hz), 7.16(1H, dd, J=2, 8 Hz), 7.45(1H, s), 9.76(1H, s).

Production Example 17

Production of methyl (E)-3-(4-chloro-1-(2,4-dichlorobenzyl)-2-methylimidazol-5-yl)-2-propenoate Methyl (E)-3-(4-chloro-1-(2,4-dichlorobenzyl)-2-methylimidazol-5-yl)-2-propenoate(289 mg) was obtained as pale-yellow crystals from 253 mg of 4-chloro-1-(2,4-dichlorobenzyl)-2-methylimidazole-5-carboxaldehyde in the same manner as in Production Example 10.
Properties of the compound:
$^1$H-NMR(CDCl$_3$): 2.33(3H, s), 3.75(3H, s), 5.17(2H, s), 6.40(1H, d, J=8 Hz), 6.48(1H, d, J=15 Hz), 7.18(1H, dd, J=2, 8 Hz), 7.28(1H, d, J=15 Hz), 7.48(1H, d, J=2 Hz).

Production Example 18

Production of (E)-3-(4-chloro-1-(2,4-dichlorobenzyl)-2-methylimidazol-5-yl)-2-propenoic acid (E)-3-(4-chloro-1-(2,4-dichlorobenzyl)-2-methylimidazol-5-yl)-2-propenoic acid (242 mg) was obtained as white crystals from 270 mg of methyl (E)-3-(4-chloro-1-(2,4-dichlorobenzyl)-2-methylimidazol-5-yl)-2-propenoate in the same manner as in Production Example 11.
Properties of the compound:
$^1$H-NMR(DMSO-d6): 2.32(3H, s), 5.40(2H, s), 6.25(1H, d, J=15 Hz), 6.53(1H, d, J=8 Hz), 7.20(1H, d, J=15 Hz), 7.39(1H, dd, J=2, 8 Hz), 7.75(1H, d, J=3 Hz).

EXAMPLE 7

Synthesis of (E)-3-(4-chloro-1-(2,4-dichlorobenzyl)-2-methylimidazol-5-yl)-N-(n-pentanesulfonyl)-2-propenamide (37)

(E)-3-(4-chloro-1-(2,4-dichlorobenzyl)-2-methyl-imidazol-5-yl)-N-(n-pentanesulfonyl)-2-propenamide (37) (142 mg) was obtained as white crystals from 130 mg of (E)-3-(4-chloro-1-(2,4-dichlorobenzyl)-2-methylimidazol-5-yl)-2-propenoic acid in the same manner as in Example 4.
Properties of compound (37):
$^1$H-NMR(DMSO-d6): 0.92(3H, t, J=7 Hz), 1.20–1.38(4H, m), 1.57–1.68(2H, m), 2.31(3H, s), 3.32–3.40(2H, m), 5.38 (2H, s), 6.51(1H, d, J=8 Hz), 6.67(1H, d, J=15 Hz), 7.26(1H, d, J=15 Hz), 7.38(1H, dd, J=2, 8 Hz), 7.74(1H, d, J=2 Hz).

EXAMPLE 8

Synthesis of (E)-3-(4-chloro-1-(2,4-dichlorobenzyl)-2-methylimidazol-5-yl)-N-benzenesulfonyl-2-propenamide (38)

(E)-3-(4-chloro-1-(2,4-dichlorobenzyl)-2-methylimidazol-5-yl)-N-benzenesulfonyl-2-propenamide (38) (78 mg) was obtained as white crystals from 100 mg of (E)-3-(4-chloro-1-(2,4-dichlorobenzyl)-2-methylimidazol-5-yl)-2-propenoic acid in the same manner as in Example 4.
Properties of compound (38):
$^1$H-NMR(DMSO-d6): 2.27(3H, s), 5.33(2H, s), 6.45(1H, d, J=8 Hz), 6.60(1H, d, J=15 Hz), 7.13(1H, d, J=15 Hz), 7.34(1H, dd, J=2, 8 Hz), 7.55–7.72(4H, m), 7.90(2H, d, J=8 Hz)
Mass(ESI): m/e 484(M–H).

Production Example 19

Production of 1-(2,4-dichlorobenzyl)-2-methyl-4-phenylimidazole-5-carboxaldehyde Fifty milligrams of tetrakis(triphenylphosphine) palladium (0) were suspended in 3 ml of toluene, and 300 mg of 4-bromo-1-(2,4-dichlorobenzyl)-2-methylimidazole-5-carboxaldehyde was added thereto. After the mixture was stirred at room temperature for 10 minutes, ethanol (0.5 ml) containing 126 mg of phenylboric acid and 2M sodium carbonate aqueous solution (0.90 ml) was added thereto, and the resulting reaction mixture was heated under reflux for 8 hours. The mixture was washed with a sodium chloride aqueous solution, and the organic layer was dried over anhydrous magnesium sulfate. The solvent was then evaporated under reduced pressure. The resulting residue was purified by silica-gel column chromatography (eluent, hexane:ethyl acetate=3:1). After hexane was added to the purified material, the resulting crystals were filtered and heated to dryness under reduced pressure to yield 298 mg of pale-yellow crystals of 1-(2,4-dichlorobenzyl)-2-methyl-4-phenylimidazole-5-carboxaldehyde.
Properties of the compound:
$^1$H-NMR(CDCl$_3$): 2.42(3H, s), 5.67(2H, s), 6.49(1H, d, J=8 Hz), 7.15(1H, dd, J=2, 8 Hz), 7.45–7.50(4H, m), 7.67–7.70(2H, m), 9.82(1H, s).

Production Example 20

Production of methyl (E)-3-(1-(2,4-dichlorobenzyl)-2-methyl-4-phenylimidazol-5-yl)-2-propenoate Methyl (E)-3-(1-(2,4-dichlorobenzyl)-2-methyl-4-phenylimidazol-5-yl)-2-propenoate (288 mg) was obtained as pale-yellow crystals from 280 mg of 1-(2,4-dichlorobenzyl)-2-methyl-4-phenylimidazole-5-carboxaldehyde in the same manner as in Production Example 10.
Properties of the compound:
$^1$H-NMR(CDCl$_3$): 2.40(3H, s), 3.69(3H, s), 5.25(2H, s), 5.77(1H, d, J=15 Hz), 6.53(1H, d, J=8 Hz), 7.21(1H, dd, J=2, 8 Hz), 7.33–7.47(3H, m), 7.50(1H, d, J=3 Hz), 7.60–7.66 (3H, m).

Production Example 21

Production of (E)-3-(1-(2,4-dichlorobenzyl)-2-methyl-4-phenylimidazol-5-yl)-2-propenoic acid (E)-3-(1-(2,4-dichlorobenzyl)-2-methyl-4-phenylimidazol-5-yl)-2-propenoic acid (228 mg) was obtained as white crystals from 263 mg of methyl (E)-3-(1-(2,4-dichlorobenzyl)-2-methyl-4-phenylimidazol-5-yl)-2-propenoate in the same manner as in Production Example 11.
Properties of the compound:
$^1$H-NMR(DMSO-d6): 2.40(3H, s), 5.38(2H, s), 5.66(1H, d, J=15 Hz), 6.57(1H, d, J=8 Hz), 7.34–7.48(5H, m), 7.55–7.58(2H, m), 7.78(1H, s).

EXAMPLE 9

Synthesis of (E)-3-(1-(2,4-dichlorobenzyl)-2-methyl-4-phenylimidazol-5-yl)-N-(n-pentanesulfonyl)-2-propenamide (39)

(E)-3-(1-(2,4-dichlorobenzyl)-2-methyl-4-phenylimidazol-5-yl)-N-(n-pentanesulfonyl)-2-propenamide (39) (105 mg) was obtained as white crystals from 110 mg of (E)-3-(1-(2,4-dichlorobenzyl)-2-methyl-4-phenylimidazol-5-yl)-2-propenoic acid in the same manner as in Example 4.
Properties of compound (39):
$^1$H-NMR(DMSO-d6): 0.80(3H, t, J=7 Hz), 1.18–1.37(4H, m), 1.55–1.64(2H, m), 2.32(3H, s), 3.33–3.38(2H, m), 5.35 (2H, s), 6.02(1H, d, J=15 Hz), 6.56(1H, d, J=8 Hz), 7.37–7.57(7H, m), 7.77(1H, d, J=2 Hz).
Mass(ESI): m/e 518(M–H).

EXAMPLE 10

Synthesis of (E)-3-(1-(2,4-dichlorobenzyl)-2-methyl-4-phenylimidazol-5-yl)-N-benzenesulfonyl-2-propenamide (40)

(E)-3-(1-(2,4-dichlorobenzyl)-2-methyl-4-phenylimidazol-5-yl)-N-benzenesulfonyl-2-propenamide (40) (111 mg) was obtained as white crystals from 108 mg of (E)-3-(1-(2,4-dichlorobenzyl)-2-methyl-4-phenylimidazol-5-yl)-2-propenoic acid in the same manner as in Example 4.

Properties of compound (40):
$^1$H-NMR(DMSO-d6): 2.30(3H, s), 5.32(2H, s), 5.97(1H, d, J=15 Hz), 6.54(1H, d, J=8 Hz), 7.35–7.70(10H, m), 7.78(1H, d, J=2 Hz), 7.87(2H, d, J=7 Hz).
Mass(ESI): m/e 524(M−H).

Production Example 22

Production of 2-methy-1-(2-(trimethylsilyl)ethoxymethyl)imidazole

2-Methy-1-(2-(trimethylsilyl)ethoxymethyl)imidazole (13.2 g) was obtained as brown oily material from 5.00 g of 2-methylimidazole in the same manner as in Production Example 6.

Properties of the compound:
$^1$H-NMR(CDCl$_3$): 0.00(9H, s), 0.91(2H, t, J=8 Hz), 2.45 (9H, s), 3.50(2H, t, J=8 Hz), 5.20(2H, s), 6.92(2H, s).

Production Example 23

Production of 2-methy-1-(2-(trimethylsilyl)ethoxymethyl)imidazole-5-carboxyaldehyde 2-Methyl-1-(2-(trimethylsilyl)ethoxymethyl)imidazole-5-carboxyaldehyde (650 mg) was obtained as pale-yellow oily material from 7.00 g of 2-methy-1-(2-(trimethylsilyl)ethoxymethyl)imidazole in the same manner as in Production Example 7.

Properties of the compound:
$^1$H-NMR(CDCl$_3$): 0.00(9H, s), 0.92(2H, t, J=8 Hz), 2.57 (3H, s), 3.61(2H, s, J=8 Hz), 5.77(2H, s), 9.70(1H, s).

Production Example 24

Production of methyl (E)-3-(2-methyl-1-(2-(trimethylsilyl)ethoxymethyl)imidazol-5-yl)-2-propenoate Methyl (E)-3-(2-methy-1-(2-(trimethylsilyl)ethoxymethyl)imidazol-5-yl)-2-propenoate (656 mg) was obtained as brown powder from 634 mg of 2-methy-1-(2-(trimethylsilyl)ethoxymethyl)imidazole-5-carboxyaldehyde in the same manner as in Production Example 10.

Properties of the compound:
$^1$H-NMR (CDCl$_3$): −0.01(9H, s), 0.92(2H, t, J=8 Hz), 2.50(3H, s), 3.51(2H, d, J=8 Hz), 3.80(3H, s), 5.28(2H, s), 6.30(1H, d, J=15 Hz), 7.38(1H, s), 7.58(1H, d, J=15 Hz).
Mass(ESI): m/e 297(M+1).

Production Example 25

Production of methyl (E)-3-(2-methylimidazol-4-yl)-2-propenoate

Methyl (E)-3-(2-methylimidazol-4-yl)-2-propenoate (214 mg) was obtained as brown crystals from 653 mg of methyl (E)-3-(2-methy-1-(2-(trimethylsilyl)ethoxymethyl)imidazol-5-yl)-2-propenoate in the same manner as in Production Example 8.

Properties of the compound:
$^1$H-NMR(DMSO-d6): 2.42(3H, s), 3.70(3H,s),6.43(1H, d, J=15 Hz), 7.50(1H, d, J=15 Hz), 7.60(1H, s).
Mass(ESI): m/e 167(M+1).
mp: 200–203° C.

Production Example 26

Production of methyl (E)-3-(1-(2,4-dichlorobenzyl)-2-methyimidazol-4-yl)-2-propenoate Methyl (E)-3-(1-(2,4-dichlorobenzyl)-2-methylimidazol-4-yl)-2-propenoate(254 mg) was obtained as colorless crystals from 190 mg of methyl (E)-3-(2-methylimidazol-4-yl)-2-propenoate in the same manner as in Production Example 9.

Properties of the compound:
$^1$H-NMR (CDCl$_3$): 2.46(3H, s), 3.77(3H, s), 5.10(2H, s), 6.55(1H, d, J=15 Hz), 6.68(1H, d, J=8 Hz), 7.00(1H, s), 7.22(1H, dd, J=8, 2 Hz), 7.47(1H, brs), 7.50(1H, d, J=15 Hz).
Mass(ESI): m/e 325(M+1).
mp: 135–137° C.

Production Example 27

Production of (E)-3-(1-(2,4-dichlorobenzyl)-2-methylimidazol-4-yl)-2-propenoic acid (E)-3-(1-(2,4-dichlorobenzyl)-2-methylimidazol-4-yl)-2-propenoic acid (309 mg) was obtained as pale-brown crystals from 258 mg of methyl (E)-3-(1-(2,4-dichlorobenzyl)-2-methylimidazol-4-yl)-2-propenoate in the same manner as in Production Example 11.

Properties of the compound:
$^1$H-NMR(DMSO-d6): 2.27(3H, s), 5.22(2H, s), 6.21(1H, d, J=15 Hz), 6.90(1H, d, J=8 Hz), 7.37(1H, d, J=15 Hz), 7.42–7.49(2H, m), 7.71(1H, d, J=2 Hz).
Mass(ESI): m/e 309(M−1).
mp: 134–135° C.

EXAMPLE 11

Synthesis of (E)-3-(1-(2,4-dichlorobenzyl)-2-methylimidazol-4-yl))-N-(n-pentanesulfonyl)-2-propenamide (41)

(E)-3-(1-(2,4-dichlorobenzyl)-2-methylimidazol-4-yl))-N-(n-pentanesulfonyl)-2-propenamide (41) (220 mg) was obtained as pale-yellow crystals from 210 mg of (E)-3-(1-(2,4-dichlorobenzyl)-2-methylimidazol-4-yl-2-propenoic acid in the same manner as in Example 4.

Properties of compound (41):
$^1$H-NMR (CDCl$_3$): 0.89(3H, br t, J=7 Hz), 1.25–1.45(4H, m), 1.71–1.86(2H, m), 2.39(3H, s), 3.46(3H, br t, J=7 Hz), 5.10(2H, s), 6.61(1H, d, J=15 Hz), 6.75(1H, d, J=8 Hz), 7.05(1H, s), 7.23(1H, overlapped with CDCl$_3$), 7.47(1H, d, J=2 Hz), 7.60(1H, d, J=15 Hz).
Mass(ESI): m/e 442(M−1).
mp 170–172° C.

EXAMPLE 12

Synthesis of (E)-3-(1-(2,4-dichlorobenzyl)-2-methylimidazol-4-yl))-N-(n-pentanesulfonyl) propionamide (42)

(E)-3-(1-(2,4-dichlorobenzyl)-2-methylimidazol-4-yl))-N-(n-pentanesulfonyl) propionamide (42) (220 mg) was obtained as colorless crystals from 150 mg of (E)-3-(1-(2,4-dichlorobenzyl)-2-methylimidazol-4-yl)-N-(n-pentanesulfonyl)-2-propenamide in the same manner as in Example 5.

Properties of compound (42):
$^1$H-NMR (CDCl$_3$): 0.89(3H, br t, J=7 Hz), 1.26–1.49(4H, m), 1.78–1.90(2H,m), 2.39(3H, s), 2.68–2.75(2H, m), 2.80–2.89(2H, m), 3.41(3H, br t, J=7 Hz), 5.05(2H, s), 6.56(1H, s), 6.71(1H, d, J=8 Hz), 7.24(1H, d, J=8 Hz), 7.45(1H, d, J=2 Hz).

Mass(ESI): m/e 446(M+1).

mp: 120–122° C.

Production Example 28

Production of (E)-4-methyl-2-(4-phenylphenyl)ethenylpyridine

A mixture of 4-phenylbenzaldehyde (6.45 g), 2,4-lutidine (7.59 g), and acetic anhydride (10 ml) was heated in a bath at 150° C. for 12 hours and then heated under reflux for 12 hours. The reaction mixture was concentrated to dryness under reduced pressure, and the resulting residue was purified by silica-gel column chromatography (eluent, hexane-:ethyl acetate=9:1 to 5:1) to give 4.35 g of yellow solid material of (E)-4-methyl-2-(4-phenylphenyl)ethenylpyridine.

Properties of the compound:
$^1$H-NMR(CDCl$_3$): 2.38(3H, s), 6.98(1H, d, J=5 Hz), 7.12–7.28(2H), 7.34(1H, t, J=8 Hz), 7.44(2H, t, J=8 Hz), 7.56–7.71(7H), 8.47(1H, d, J=5 Hz)

Production Example 29

Production of (E)-2-(4-phenylphenyl)ethenylpyridine-4-carboxylic acid

A mixture of (E)-4-methyl-2-(4-phenylphenyl)ethenylpyridine (4.24 g), selenium dioxide (2.08 g), and pyridine (43 ml) was heated under reflux for 24 hours. The reaction mixture was concentrated to dryness under reduced pressure, and the resulting residue was extracted with a mixture of chloroform, methanol, and aqueous ammonium (65:25:4). The extract was concentrated to dryness under reduced pressure, and the resulting residue was ground in ethyl acetate to give 3.81 g of brown powder of (E)-2-(4-phenylphenyl)ethenylpyridine-4-carboxylic acid.

Properties of the compound:
$^1$H-NMR(DMSO-d6): 7.32–7.53(4H), 7.63(1H, d, J=5 Hz), 7.70–7.84(8H), 7.96(1H, s), 8.66(1H, d, J=5 Hz).

EXAMPLE 13

Synthesis of N-(n-pentanesulfonyl)-2-((E)-(4-phenylphenyl)ethenylpyridine-4-carboxyamide (43)

(E)-2-(4-phenylphenyl)ethenylpyridine-4-carboxylic acid (277 mg) was dissolved in 2.8 ml of dry dimethylformamide, and 194 mg of N,N'-carbonyldiimidazole was added thereto. The mixture was stirred at room temperature for 1.5 hours and then stirred at 100° C. for 30 minutes. After being cooled down to room temperature, the mixture was mixed with 209 mg of pentanesulfonamide and 210 mg of 1,8-diazabicyclo[5.4.0]undec-7-ene. The reaction mixture was stirred at 100° C. for 48 hours. The mixture was then cooled with ice, and its pH was adjusted to 5 using 1N hydrochloric acid. The resulting precipitate was collected by filtration and washed with water. The partially purified material thus obtained was further purified by silica-gel thin-layer chromatography (eluent, chloroform:methanol:water=65:25:4) to yield 67 mg of brown powder of N-(n-pentanesulfonyl)-2-((E)-(4-phenylphenyl)ethenylpyridine-4-carboxyamide (43).

Properties of compound (43):
$^1$H-NMR(DMSO-d6): 0.85(3H, t, J=6 Hz), 1.30(4H, m), 1.64(2H, m), 3.22(2H, t, J=6 Hz), 7.32–7.53(4H), 7.62–7.86(8H), 7.98(1H, s), 8.63(1H, d, J=5 Hz).

Production Example 30

Production of (E)-4-methyl-2-(4-phenylphenyl)ethenylpyridine

A mixture of 4-phenylbenzaldehyde (6.45 g), 2,4-lutidine (7.59 g), and acetic anhydride (10 ml) was heated on a bath at 150° C. for 12 hours and then heated under reflux for 12 hours. The reaction mixture was concentrated to dryness under reduced pressure, and the resulting residue was purified by silica-gel column chromatography (eluent, hexane-:ethyl acetate=9:1 to 5:1) to give 4.35 g of a yellow solid of (E)-4-methyl-2-(4-phenylphenyl)ethenylpyridine.

Properties of the compound:
$^1$H-NMR(CDCl$_3$): 2.38(3H, s), 6.98(1H, d, J=5 Hz), 7.12–7.28(2H), 7.34(1H, t, J=8 Hz), 7.44(2H, t, J=8 Hz), 7.56–7.71(7H), 8.47(1H, d, J=5 Hz).

Production Example 31

Production of (E)-2-(4-phenylphenyl)ethenylpyridine-4-carboxylic acid

A mixture of (E)-4-methyl-2-(4-phenylphenyl)ethenylpyridine (4.24 g), selenium dioxide (2.08 g), and pyridine (43 ml) was heated under reflux for 24 hours. The reaction mixture was concentrated to dryness under reduced pressure, and the resulting residue was extracted with a mixture of chloroform, methanol, and aqueous ammonium (65:25:4). The extract was concentrated to dryness under reduced pressure, and the resulting residue was ground in ethyl acetate to give 3.81 g of brown powder of (E)-2-(4-phenylphenyl)ethenylpyridine-4-carboxylic acid.

Properties of the compound:
$^1$H-NMR(DMSO-d6): 7.32–7.53(4H), 7.63(1H, d, J=5 Hz), 7.70–7.84(8H), 7.96(1H, s), 8.66(1H, d, J=5 Hz).

Production Example 32

Production of (E)-N-(n-pentanesulfonyl)-2-(2-(4-phenylphenyl)ethenyl)pyridine-4-carboxyamide (E)-2-(2-(4-phenylphenyl)ethenyl)pyridine-4-carboxylic acid (277 mg) was dissolved in 2.8 ml of dried dimethylformamide, and 194 mg of carbonyldiimidazole was added thereto. The mixture was stirred at room temperature for 1.5 hours and then stirred at 100° C. for 30 minutes. After being cooled to room temperature, the mixture was mixed with 209 mg of pentanesulfonamide and 210 mg of 1,8-diazabicyclo[5.4.0]undec-7-ene and stirred at 100° C. for 48 hours. The reaction mixture was cooled with ice, and then its pH was adjusted to 5 using 1N hydrochloric acid. The resulting precipitate was collected by filtration and washed with water. The partially purified material thus obtained was further purified by silica-gel thin-layer chromatography (eluent, chloroform:methanol:water=65:25:4) to yield 67 mg of brown powder of (E)-N-(n-pentanesulfonyl)-2-(2-(4-phenylphenyl)ethenyl)pyridine-4-carboxyamide.

Properties of the compound:
¹H-NMR(DMSO-d6): 0.85(3H, t, J=6 Hz), 1.30(4H, m), 1.64(2H, m), 3.22(2H, t, J=6 Hz), 7.32–7.53(4H), 7.62–7.86 (8H), 7.98(1H, s), 8.63(1H, d, J=5 Hz).

Production Example 33

Production of methyl 3-(1-(2,4-dichlorobenzyl)-2-methylimidazol-5-yl)-3-hydroxy-2-(thiophen-2-ylmethyl)propionate Diisopropylamine (338 mg) was dissolved in 2 ml of tetrahydrofuran, and 2.10 ml of hexane containing 1.6M n-butyllithium was added to the mixture. It was cooled on a dry ice-acetone bath using a syringe under a nitrogen atmosphere and stirred for 30 minutes on an ice-water bath. One milliliter of tetrahydrofuran containing 285 mg of methyl 3-(2-thienyl)propionate was added to the mixture, which was cooled on a dry ice-acetone bath and stirred for 1 hour. Then, 2 ml of tetrahydrofuran containing 1-(2,4-dichlorobenzyl)-2-methylimidazole-5-carboxyaldehyde (300 mg) was added thereto with a syringe. After being stirred for 1 hour, a saturated ammonium chloride aqueous solution and ethyl acetate were added thereto, and then the dry ice-acetone bath was removed. The reaction mixture was mixed with water and extracted with ethyl acetate. The organic layer was washed with a saturated sodium chloride aqueous solution, dried over anhydrous magnesium sulfate, and filtrated. The filtrate was concentrated under reduced pressure to give 490 mg of brown oily crude product of methyl 3-(1-(2,4-dichlorobenzyl)-2-methylimidazol-5-yl)-3-hydroxy-2-(thiophen-2-ylmethyl)propionate.

Production Example 34

Production of methyl (E)-3-(1-(2,4-dichlorobenzyl)-2-methylimidazol-5-yl)-2-(thiophen-2-ylmethyl)-2-propenoate Methyl 3-(1-(2,4-dichlorobenzyl)-2-methylimidazol-5-yl)-3-hydroxy-2-(thiophen-2-ylmethyl)propionate (490 mg) obtained in the process of Production Example 33 was dissolved in 5 ml of dichloromethane, and 683 mg of acetic anhydride and 55 mg of 4-(dimethylamino)pyridine were added thereto. The mixture was stirred at room temperature overnight. A saturated sodium hydrogen carbonate aqueous solution was then added thereto, and the mixture was stirred for 30 minutes. The solution was extracted twice with dichloromethane, dried over anhydrous sodium sulfate, and filtered. The filtrate was concentrated under reduced pressure. The resulting residue was dissolved in 5 ml of toluene, and 424 mg of 1,8-diazabicyclo[5.4.0]undec-7-ene was added thereto. The mixture was heated at 100° C. on an oil bath for 1 hour, and then concentrated under reduced pressure. A saturated ammonium chloride aqueous solution and ethyl acetate were added to the concentrate, the organic layer was washed with a saturated sodium chloride aqueous solution and dried over anhydrous sodium sulfate followed by filtration. The filtrate was concentrated under reduced pressure, and the resulting residue was subjected to silica-gel column chromatography and eluted with a mixture of hexane and ethyl acetate (1:3). The desired fractions were collected and concentrated under reduced pressure to yield 111 mg of white crystals of methyl (E)-3-(1-(2,4-dichlorobenzyl)-2-methylimidazol-5-yl)-2-(thipheh-2-ylmethyl)-2-propenoate.
Properties of the compound:
¹H-NMR(CDCl₃): 2.34(3H, s), 3.73(3H, s), 4.12(2H, s), 5.17(2H, s), 6.30(1H, d, J=8 Hz), 6.80(1H, d, J=3 Hz), 6.90(1H, t, J=6 Hz), 7.35(1H, s), 7.41(1H, s), 7.46(1H, d, J=2 Hz).

Production Example 35

Production of (E)-3-(1-(2,4-dichlorobenzyl)-2-methyl-imidazol-5-yl)-2-(thiophen-2-ylmethyl)-2-propenoic acid White crystals of (E)-3-(1-(2,4-dichlorobenzyl)-2-methylimidazol-5-yl)-2-(thiophen-2-yl-methyl)-2-propenoic acid (100 mg) were obtained from 101 mg of methyl (E)-3-(1-(2,4-dichlorobenzyl)-2-methylimidazol-5-yl)-2-(thiophen-2-ylmethyl)-2-propenoate obtained in Production Example 34 in the same manner as in Production Example 11.
Properties of the compound:
¹H-NMR(DMSO-d6): 2.30(3H, s), 3.97(2H,s), 5.32(2H, s), 6.38(1H, d, J=8 Hz), 6.79(1H, d, J=2 Hz), 6.93(1H, t, J=3 Hz), 7.25–7.27(3H, m), 7.36(1H, d, J=8 Hz), 7.72(1H, d, J=2 Hz).

EXAMPLE 14

Synthesis of (E)-3-(1-(2,4-dichlorobenzyl)-2-methyl-imidazol-5-yl)-N-(n-pentanesulfonyl)-2-((thiophen-2-yl)methyl)-2-propenamide (44)

White crystals of (E)-3-(1-(2,4-dichlorobenzyl)-2-methylimidazol-5-yl)-N-(n-pentanesulfonyl)-2-((thiophen-2-yl)methyl)-2-propenamide (74 mg) were obtained from 85 mg of (E)-3-(1-(2,4-dichlorobenzyl)-2-methylimidazol-5-yl)-2-(thiophen-2-ylmethyl)-2-propenoic acid obtained in Production Example 35 and 47 mg of 1-pentanesulfonamide in the same manner as in Example 4.
Properties of the compound:
¹H-NMR(DMSO-d6): 0.89(3H, t, J=7 Hz), 1.12–1.30(4H, m), 1.46–1.56(2H, m), 2.23(3H, s), 3.23–3.40(2H, m), 4.03 (2H, s), 5.40(2H, s), 6.33(1H, d, J=8 Hz), 6.81(1H, d, J=2 Hz), 6.93(1H, t, J=3 Hz), 7.21(1H, s), 7.26–7.37(4H, m), 7.72(1H, d, J=2 Hz).

Production Example 36

Production of ethyl 2-benzyl-3-(1-(2,4-dichlorobenzyl)-2-methylimidazol-5-yl)-3-hydroxypropionate A brown oily crude product of ethyl 2-benzyl-3-(1-(2,4-dichlorobenzyl)-2-methylimidazol-5-yl)-3-hydroxypropionate (499 mg) were obtained starting from 300 mg of 1-(2,4-dichlorobenzyl)-2-methylimidazole-5-carboxyaldehyde and 298 mg of ethyl 3-phenylpropionate in the same manner as in Production Example 33.

Production Example 37

Production of ethyl (E)-2-benzyl-3-(1-(2,4-dichlorobenzyl-2-methylimidazol-5-yl)-2-propenoate White crystals of ethyl (E)-2-benzyl-3-(1-(2,4-dichlorobenzyl)-2-methylimidazol-5-yl)-2-propenoate (70 mg) were obtained from 499 mg of ethyl 2-benzyl-3-(1-(2,4-dichlorobenzyl)-2-methylimidazol-5-yl)-3-hydroxypropionate obtained in Production Example 36 in the same manner as in Production Example 34.
Properties of the compound:
¹H-NMR(CDCl₃): 1.18(3H, t, J=7 Hz), 2.34(3H, s), 3.97 (2H, s), 4.13(2H, q, J=8 Hz), 5.18(2H, s), 6.32(1H, d, J=8 Hz), 7.11–7.27(7H, m), 7.40(1H, s), 7.47 (1H, s).

Production Example 38

Production of (E)-2-benzyl-3-(1-(2,4-dichlorobenzyl)-2-methylimidazol-5-yl)-2-propenoic acid White crystals of (E)-2-benzyl-3-(1-(2,4-dichlorobenzyl)-2-methylimidazol-5-yl)-2-propenoic acid (50 mg) were obtained from 57 mg of ethyl (E)-2-benzyl-3-(1-(2,4-dichlorobenzyl)-2-methylimidazol-5-yl)-2-propenoate that was obtained in Production Example 37 in the same manner as in Production Example 11.

Properties of the compound:
$^1$H-NMR(DMSO-d6): 2.29(3H, s), 3.83(2H, s), 5.33(2H, s), 6.40(1H, d, J=8 Hz), 7.05–7.08(3H, m), 7.15(1H, t, J=7 Hz), 7.26(1H, t, J=7 Hz), 7.36–7.40(2H, m), 7.72(1H, d, J=2 Hz).

EXAMPLE 15

Synthesis of (E)-2-benzyl-3-(1-(2,4-dichlorobenzyl)-2-methylimidazol-5-yl)-N-(n-pentanesulfonyl)-2-propenamide (45)

White crystals of (E)-2-benzyl-3-(1-(2,4-dichlorobenzyl)-2-methylimidazol-5-yl)-N-(n-pentanesulfonyl)-2-propenamide (25 mg) were obtained from 42 mg of (E)-2-benzyl-3-(1-(2,4-dichlorobenzyl)-2-methyl-imidazol-5-yl)-2-propenoic acid and 24 mg of 1-pentanesufonamide in the same manner as in Example 4.

Properties of the compound:
$^1$H-NMR(DMSO-d6): 0.78(3H, t, J=7 Hz), 1.07–1.27(4H, m), 1.40–1.50(2H, m), 2.22(3H, s), 3.21–3.40(2H, m), 3.90 (2H, s), 5.40(2H, s), 6.32(1H, d, J=8 Hz), 7.08–7.10(3H, m), 7.17(1H, t, J=7 Hz), 7.25–7.30(3H, m), 7.38(1H, d, J=8 Hz), 7.72(1H, d, J=2 Hz).

Test Example

Test for Activity of Decreasing Plasma Glucose Level Using db/db Mice

Test Compound (E)-3-(4-bromo-1-(2,4-dichlorobenzyl)-2-methyl-imidazol-5-yl)-N-(n-pentanesulfonyl)-2-propenamide (33)

Animal Used

Five-week-old female mice [C57BL/KsJ-dbm db+/db+, C57BL/KsJ-dbm +m/+m (Jackson Laboratory)] were purchased, and were kept for 2 to 3 weeks. Then, these mice were used in the test.

Preparation of the Agent

The test compound was mixed with a powdered chow (CE-2, made by Nippon Clea) using a mortar. The mixing ratio was 0.01%. The mixed chow was changed twice a week. The feed amount and the remaining amount were recorded, and the intake was calculated from the difference therebetween.

Test Schedule

The female db/db mice were grouped according to the body weight, the plasma glucose level and the plasma triglyceride concentration. Then, the mixture containing the test compound was administered to the mice (8- to 10-week-old) for 14 days. In the morning on day 7 and day 14, the blood was collected from the orbital venous plexus using heparinized glass capillary tubes (Chase Heparinized Capillary Tubes), and a plasma fraction was obtained through centrifugal separation. Plasma glucose, triglyceride, and insulin concentrations were measured on day 0 and day 14 as well as plasma glucose and triglyceride concentrations on day 7. The body weight was measured on day 0, day 7, and day 14. After the final collection of the blood, the mice were sacrificed using $CO_2$ gas.

Measurement Method

The plasma glucose was measured by a glucose oxidase method (Glucose CII-Test Wako made by Wako Pure Chemical Industries, Ltd.) using 10 to 15 μl of plasma. The plasma triglyceride concentration was measured by a GPO-p-chloro-phenol method (Triglyceride G-Test Wako made by Wako Pure Chemical Industries, Ltd.) or a GPO-DAOS method (Triglyceride E-Test Wako) using 10 to 15 μl of plasma. The above-mentioned measurements were performed immediately after the blood collection. The plasma insulin concentration was measured by an immunological method (Phadesef Insulin RIA Kit made by Cabi Pharmacia) using 20 μl of plasma (which can be stored at −20° C.).

Results

The difference in the plasma glucose level or in the plasma triglyceride concentration between a control group of the db/db mice and a group of the +/+ mice was defined as 100%, and the rate (%) of decrease in the plasma glucose level or the plasma triglyceride concentration of the group to which the test compound was administered was calculated. When 10 mg of the test compound was administered to a mouse per kg of body weight, activities of decreasing plasma glucose and plasma triglyceride were 60% and 104%, respectively.

Industrial Applicability

Novel aromatic ring derivatives and their pharmaceutically acceptable salts are provided. The compounds and their salts have blood sugar level-depressing activity or PDE5-inhibiting activity, and are useful for preventing and treating impaired glucose tolerance, diabetes (type II diabetes), diabetic complications (e.g., diabetic gangrene, diabetic arthropathy, diabetic osteopenia, diabetic glomerulosclerosis, diabetic nephropathy, diabetic dermatopathy, diabetic neuropathy, diabetic cataract, diabetic retinopathy, etc.), syndrome of insulin resistance (e.g., insulin receptor disorders, Rabson-Mendenhall syndrome, leprechaunism, Kobberling-Dunnigan syndrome, Seip syndrome, Lawrence syndrome, Cushing syndrome, acromegaly, etc.), polycystic ovary syndrome, hyperlipidemia, atherosclerosis, cardiovascular disorders (e.g., stenocardia, cardiac failure, etc.), hyperglycemia (e.g., those characterized by abnormal saccharometabolism such as feeding disorders, etc.), hypertension, stenocardia, pulmonary hypertension, congestive heart failure, glomerulopathy (e.g., diabetic glomerulosclerosis, etc.), tubulointerstitial disorders (e.g., renopathy induced by FK506, cyclosporin, etc.), renal failure, atherosclerosis, angiostenosis (e.g., after percutaneous arterioplasty), distal angiopathy, cerebral apoplexy, chronic reversible obstructions (e.g., bronchitis, asthma (chronic asthma, allergic asthma), etc.), autoimmune diseases, allergic rhinitis, urticaria, glaucoma, diseases characterized by enteromotility disorders (e.g., hypersensitive enteropathy syndrome, etc.), impotence (e.g., organic impotence, psychic impotence, etc.), nephritis, cachexia (e.g., progressive weight loss due to lipolysis, myolysis, anemia, edema, anorexia etc., in chronic diseases including cancer, tuberculosis, endocrinopathy, AIDS, etc.), pancreatitis, or restenosis after PTCA.

What is claimed is:

1. A pharmaceutical composition which comprises, as an active ingredient, a heterocyclic aromatic ring compound of formula (I):

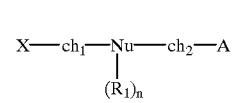

(I)

wherein X indicates the substituent represented by formula (II);

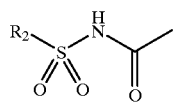

(II)

wherein R₂ represents a lower alkyl group, a lower alkenyl group, a lower alkynyl group, a cyclo-lower alkyl group, an aromatic group, a heterocyclic aromatic group, or a heterocyclic group, each of which may have one or more substituents; $ch_1$ and $ch_2$ represent a saturated or unsaturated cross-linking group, which may be branched; $ch_1$ may have one or more substituents selected from a group consisting of a lower alkyl group, a lower cycloalkyl group, an aromatic group, a heterocyclic group, a lower alkyl-lower cycloalkyl group, an aromatic-lower alkyl group, and a heterocyclic lower alkyl group; Nu represents an imidazole ring; X and Nu may be bonded directly to each other; $R_1$ represents a hydrogen atom, a halogen atom, a lower alkyl group, an amino group, an acylamino group, a lower alkenyl group, a lower alkynyl group, a halo-lower alkyl group, a lower cycloalkyl group, a nitro group, a lower alkylamino group, a carboxyl group, an esterified carboxyl group, an amidated carboxyl group, a lower alkanesulfonyl group, an aromatic-sulfonyl group, a heterocyclic-aromatic-sulfonyl group, a hydroxyl group, or a lower alkoxyl group; n means a natural number of 2 or less; and A is an aromatic ring that may have one or more substituents; or its pharmaceutically acceptable salt.

2. The pharmaceutical composition of claim 1, wherein the heterocyclic aromatic ring compound is represented by formula (I) where $ch_1$ is an ethylene chain or an ethenylene chain; $ch_2$ is a methylene chain; and $R_1$ is a hydrogen atom, a lower alkyl group, a halogen atom, or a phenyl group.

3. The pharmaceutical composition of claim 2, wherein the heterocyclic aromatic ring compound is represented by formula (V) or formula (VI):

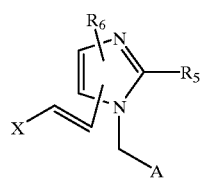

(V)

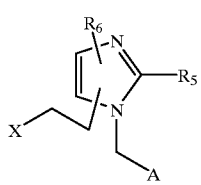

(VI)

wherein R₅ represents a hydrogen atom or a lower alkyl group; R₆ is a hydrogen atom, a halogen atom, or a phenyl group; and X and A are as defined above.

4. The pharmaceutical composition of claim 1, wherein the aromatic ring compound is represented by formula (I) where X is a lower alkylsulfonylcarbamoyl group, a lower alkenylsulfonylcarbamoyl group, a lower alkynylsulfonylcarbamoyl group, an aromatic-sulfonylcarbamoyl group, a heterocyclic sulfonylcarbamoyl group, or a heterocyclic-aromatic-sulfonylcarbamoyl group, each of which may have one or more substituents.

5. A heterocyclic aromatic ring compound represented by formula (I):

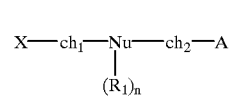

(I)

wherein X indicates the substituent represented by formula (II):

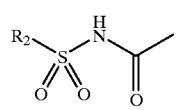

(II)

wherein R₂ is a lower alkyl group, a lower alkenyl group, a lower alkynyl group, a cyclo-lower alkyl group, an aromatic group, a heterocyclic aromatic group, or a heterocyclic group, each of which may have one or more substituents; $ch_1$ and $ch_2$ each represents a saturated or unsaturated cross-linking group, which may be branched; $ch_1$ may have one or more substituents selected from a group consisting of a lower alkyl group, a lower cycloalkyl group, an aromatic group, a heterocyclic aromatic group, a heterocyclic group, a lower alkyl-lower cycloalkyl group, an aromatic-lower alkyl group, a heterocyclic-aromatic-lower alkyl group, and a heterocyclic lower alkyl group; Nu represents an imidazole ring; X and Nu may be bonded directly to each other; $R_1$ represents a hydrogen atom, a halogen atom, a lower alkyl group, an amino group, an acylamino group, a lower alkenyl group, a lower alkynyl group, a halo-lower alkyl group, a lower cycloalkyl group, a nitro group, a lower alkylamino group, a carboxyl group, an esterified carboxyl group, an amidated carboxyl group, a lower alkanesulfonyl group, an aromatic-sulfonyl group, a heterocyclic-aromatic-sulfonyl group, a hydroxyl group, or a lower alkoxyl group; n means a natural number of 2 or less; and A is an aromatic ring that may have one or more substituents; and its pharmaceutically acceptable salt.

6. The heterocyclic aromatic ring compound and its pharmaceutically acceptable salt of claim 5, wherein $ch_1$ is an ethylene chain or an ethenylene chain; $ch_2$ is a methylene chain; and $R_1$ is a hydrogen atom, a lower alkyl group, a halogen atom, or a phenyl group.

7. An heterocyclic aromatic ring compound represented by formula (V) or formula (VI):

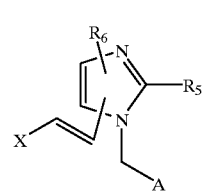

(V)

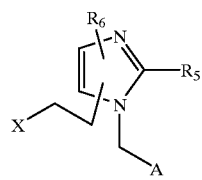

(VI)

wherein $R_5$, $R_6$, X and A are as defined above; and its pharmaceutically acceptable salt.

8. The heterocyclic aromatic ring compound and its pharmaceutically acceptable salt of claim 5, 6 or 7, wherein X is a lower alkylsulfonylcarbamoyl group, a lower alkenylsulfonylcarbamoyl group, a lower alkynylsulfonylcarbamoyl group, an aromatic-sulfonylcarbamoyl group, a heterocyclic-aromatic-sulfonylcarbamoyl group, or a heterocyclic sulfonylcarbamoyl group each of which may have one or more substituents.

9. A method for preventing or treating impaired glucose tolerance, diabetes, diabetic complications, syndrome of insulin resistance, polycystic ovary syndrome, hyperlipidemia, atherosclerosis, cardiovascular disorders, hyperglycemia, and hypertension comprising administering to a patient in need thereof an effective amount of a heterocyclic aromatic ring compound represented by formula (I):

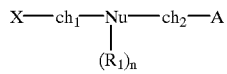

(I)

wherein x indicates the substituent represented by formula (II):

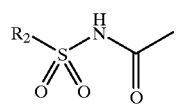

(II)

wherein $R_2$ represents a lower alkyl group, a lower alkenyl group, a lower alkynyl group, a cyclo-lower alkyl group, an aromatic group, a heterocyclic aromatic group, or a heterocyclic group, each of which may have one or more substituents; $ch_1$ and $ch_2$ represent a saturated or unsaturated cross-linking group, which may be branched; $ch_1$ may have one or more substituents selected from a group consisting of a lower alkyl group, a lower cycloalkyl group, an aromatic group, a heterocyclic aromatic group, a heterocyclic group, a lower alkyl-lower cycloalkyl group, an aromatic-lower alkyl group, a heterocyclic-aromatic-lower alkyl group, and a heterocyclic lower alkyl group; Nu represents an imidazole ring; X and Nu may be bonded directly to each other; $R_1$ represents a hydrogen atom, a halogen atom, a lower alkyl group, an amino group, an acylamino group, a lower alkenyl group, a lower alkynyl group, a halo-lower alkyl group, a lower cycloalkyl group, a nitro group, a lower alkylamino group, a carboxyl group, an esterified carboxyl group, an amidated carboxyl group, a lower alkanesulfonyl group, an aromatic-sulfonyl group, a heterocyclic-aromatic-sulfonyl group, a hydroxyl group, or a lower alkoxyl group; n means a natural number of 2 or less; and A is an aromatic ring that may have one or more substituents; or its pharmaceutically acceptable salt.

10. A method for lowering blood sugar levels, which comprises administering an effective amount of the compound of claim 5 to a patient in need thereof.

* * * * *